United States Patent
Makharinsky

(10) Patent No.: US 11,000,689 B2
(45) Date of Patent: May 11, 2021

(54) LEADLESS MULTI-ELECTRODE CARDIAC PACEMAKERS AND METHODS OF IMPLANTATION THEREOF

(71) Applicant: Eagle Point Medical LLC, City of Dover, DE (US)

(72) Inventor: Leonid Makharinsky, Tal-Pieta (MT)

(73) Assignee: Eagle Point Medical LLC, City of Dover, DE (US)

(*) Notice: Subject to any disclaimer, the term of this patent is extended or adjusted under 35 U.S.C. 154(b) by 312 days.

(21) Appl. No.: 16/221,547

(22) Filed: Dec. 16, 2018

(65) Prior Publication Data
US 2020/0016418 A1 Jan. 16, 2020

Related U.S. Application Data

(63) Continuation-in-part of application No. 16/035,653, filed on Jul. 15, 2018, now Pat. No. 10,695,558.

(51) Int. Cl.
| | | |
|---|---|---|
| *A61N 1/375* | (2006.01) | |
| *A61N 1/362* | (2006.01) | |
| *A61N 1/368* | (2006.01) | |
| *A61N 1/39* | (2006.01) | |

(52) U.S. Cl.
CPC ....... *A61N 1/37512* (2017.08); *A61N 1/3622* (2013.01); *A61N 1/3756* (2013.01); *A61N 1/368* (2013.01); *A61N 1/3627* (2013.01); *A61N 1/3956* (2013.01)

(58) Field of Classification Search
CPC .............. A61N 1/37512; A61N 1/3622; A61N 1/3756; A61N 1/3627; A61N 1/368; A61N 1/3956; A61N 1/36842; A61N 1/37518
See application file for complete search history.

(56) References Cited

U.S. PATENT DOCUMENTS

| | | |
|---|---|---|
| 5,083,564 A | 1/1992 | Scherlag |
| 5,251,643 A | 10/1993 | Osypka |
| 6,600,957 B2 | 7/2003 | Gadsby |
| 6,609,027 B2 | 8/2003 | Kroll |
| 6,684,109 B1 | 1/2004 | Osypka |
| 6,718,206 B2 | 4/2004 | Casavant |
| 6,898,465 B2 | 5/2005 | Gadsby |
| 6,907,299 B2 | 6/2005 | Han |

(Continued)

OTHER PUBLICATIONS

Deshmukh P et al. Permanent, Direct His-Bundle Pacing A Novel Approach to Cardiac Pacing in Patients With Normal His-Purkinje Activation. Circulation. 2000;101:869-877.

(Continued)

*Primary Examiner* — Mark Bockelman
(74) *Attorney, Agent, or Firm* — Boris Leschinsky

(57) ABSTRACT

A leadless cardiac pacemaker is adapted for implantation into triangle of Koch or His bundle with a plurality of individual electrodes spread in the vicinity of implantation site. Individual electrodes are first evaluated for their suitability for sensing and pacing of atrial and ventricular chambers of the heart. Individual electrodes are then selected for delivery of cardiac pacing to multiple heart chambers from a single intra-cardiac location. Remaining non-selected individual electrodes may be abandoned. Also described is an adapter with multiple electrodes configured to dock with a conventional leadless or standard pacemaker to operate in the same way.

20 Claims, 25 Drawing Sheets

(56) References Cited

U.S. PATENT DOCUMENTS

| | | |
|---|---|---|
| 6,937,897 B2 | 8/2005 | Min |
| 7,027,876 B2 | 4/2006 | Casavant |
| 7,082,335 B2 | 6/2006 | Klein |
| 7,089,045 B2 | 8/2006 | Fuimaono |
| 7,228,164 B2 | 6/2007 | Fuimaono |
| 7,245,973 B2 | 7/2007 | Liu |
| 7,302,285 B2 | 11/2007 | Fuimaono |
| 7,326,204 B2 | 2/2008 | Paul |
| 7,326,205 B2 | 2/2008 | Paul |
| 7,326,206 B2 | 2/2008 | Paul |
| 7,440,800 B2 | 10/2008 | Mower |
| 7,729,782 B2 | 6/2010 | Williams |
| 7,819,870 B2 | 10/2010 | Thao |
| 8,021,361 B2 | 9/2011 | Paul |
| 8,078,287 B2 | 12/2011 | Liu |
| 8,162,935 B2 | 4/2012 | Paul |
| 8,332,035 B2 | 12/2012 | Iaizzo |
| 8,391,995 B2 | 3/2013 | Efimov |
| 8,406,899 B2 | 3/2013 | Reddy |
| 8,428,715 B2 | 4/2013 | Ortega |
| 8,437,848 B2 | 5/2013 | Ortega |
| 8,447,399 B2 | 5/2013 | Mower |
| 8,460,286 B2 | 6/2013 | Stangenes |
| 8,538,521 B2 | 9/2013 | Zhu |
| 8,606,369 B2 | 12/2013 | Williams |
| 8,644,927 B2 | 2/2014 | Imran |
| 8,672,936 B2 | 3/2014 | Thao |
| 8,679,109 B2 | 3/2014 | Paul |
| 8,731,662 B2 | 5/2014 | Imran |
| 8,761,880 B2 | 6/2014 | Maskara |
| 8,825,155 B2 | 9/2014 | Zhu |
| 8,838,237 B1 | 9/2014 | Niazi |
| 8,942,805 B2 | 1/2015 | Shuros |
| 8,954,142 B2 | 2/2015 | Ek |
| 8,954,145 B2 | 2/2015 | Lee |
| 9,022,962 B2 | 5/2015 | Brown |
| 9,138,160 B2 | 9/2015 | Imran |
| 9,216,280 B1 | 12/2015 | Hakki |
| 9,289,593 B1 | 3/2016 | Hakki |
| 9,381,361 B2 | 7/2016 | Giovangrandi |
| 9,533,140 B2 | 1/2017 | Ek |
| 9,549,708 B2 | 1/2017 | Mercanzini |
| 9,764,142 B2 | 9/2017 | Imran |
| 2002/0082658 A1 | 6/2002 | Heinrich |
| 2002/0120318 A1 | 9/2002 | Kroll |
| 2003/0040676 A1 | 2/2003 | Prentice |
| 2003/0050637 A1 | 3/2003 | Maguire |
| 2003/0105492 A1 | 6/2003 | Ding |
| 2003/0212436 A1 | 11/2003 | Brown |
| 2004/0064176 A1 | 4/2004 | Min |
| 2005/0131464 A1 | 6/2005 | Heinrich |
| 2005/0267467 A1 | 12/2005 | Paul |
| 2008/0091192 A1 | 4/2008 | Paul |
| 2008/0140139 A1 | 6/2008 | Heinrich |
| 2009/0093859 A1 | 4/2009 | Ortega |
| 2010/0016917 A1 | 1/2010 | Efimov |
| 2010/0228308 A1 | 9/2010 | Cowan |
| 2010/0318147 A1 | 12/2010 | Forslund |
| 2011/0230922 A1 | 9/2011 | Fishel |
| 2012/0101539 A1 | 4/2012 | Zhu |
| 2013/0116740 A1 | 5/2013 | Bornzin |
| 2013/0123870 A1 | 5/2013 | Heinrich |
| 2013/0123872 A1 | 5/2013 | Bornzin |
| 2013/0158621 A1 | 6/2013 | Ding |
| 2014/0067036 A1 | 3/2014 | Shuros |
| 2014/0172035 A1 | 6/2014 | Shuros |
| 2014/0228713 A1 | 8/2014 | Thao |
| 2014/0249604 A1 | 9/2014 | Brown |
| 2014/0276929 A1 | 9/2014 | Foster |
| 2015/0094783 A1 | 4/2015 | Brown |
| 2015/0134022 A1 | 5/2015 | Lee |
| 2015/0151109 A1 | 6/2015 | Ek |
| 2016/0022998 A1 | 1/2016 | Imran |
| 2016/0136434 A1 | 5/2016 | Lee |
| 2016/0346532 A1 | 12/2016 | Shelton et al. |
| 2017/0080210 A1 | 3/2017 | Mercanzini |
| 2017/0087352 A1 | 3/2017 | Ek |
| 2017/0291022 A1 | 10/2017 | Shuros et al. |
| 2018/0214689 A1 | 8/2018 | Zhang |
| 2019/0083800 A1 * | 3/2019 | Yang et al. |

OTHER PUBLICATIONS

Temple IP et al. Connexins and the atrioventricular node. Heart Rhythm 2013;10:297-304.

Mulpuru SK et al. Synchronous ventricular pacing with direct capture of the atrioventricular conduction system: Functional anatomy, terminology, and challenges. Heart Rhythm 2016;13:2237-2246.

* cited by examiner

LEADLESS MULTI-ELECTRODE CARDIAC PACEMAKERS AND METHODS OF IMPLANTATION THEREOF

CROSS-REFERENCE DATA

This application is a continuation-in-part and claims a priority date benefit of a co-pending U.S. patent application Ser. No. 16/035,653 filed 15 Jul. 2018 by the same inventor entitled "Single conduit multi-electrode cardiac pacemaker and methods of using thereof", which is incorporated herein by reference in its entirety.

BACKGROUND OF THE INVENTION

Without limiting the scope of the invention, its background is described in connection with implantable medical devices, in particular, implantable leadless cardiac pacemakers or defibrillators. More specifically, the invention describes the single pacemaker with a plurality of electrodes located inside the heart, such cardiac pacemaker is configured for pacing one or more heart chambers from a single intra-cardiac location.

As used herein, the term "leadless" generally refers to an absence of electrically-conductive leads or wires that traverse vessels or other anatomy outside of the intra-cardiac space, while "intra-cardiac" means generally, located entirely within the heart and associated vessels, such as the superior vena cava (SVC), inferior vena cava (IVC), coronary sinus (CS), pulmonary arteries (PA) and the like. The term "His bundle" generally refers to a heart electrical signals conduction system traversing His bundle as well as further distal parts thereof including but not limited to left bundle branch and right bundle branch.

An implantable device, such as an implantable cardiac rhythm management device (e.g., a pacemaker, a defibrillator, or a cardioverter—all of which are contemplated by this disclosure and referred to generally as a "pacemaker"), may be used to monitor cardiac function and provide cardiac stimulation therapy for a patient who suffers from cardiac arrhythmia. For example, to maintain regular cardiac rhythm, the implantable device may track the type and timing of native cardiac signals. In this way, the implantable device may determine whether cardiac events (e.g., contractions) are occurring and whether they are occurring at the proper times.

The implantable heart rhythm management device may track cardiac signals and provide suitable cardiac pacing stimulation by using one or more leads implanted in or near the heart of the patient. For example, the implantable device may process signals received via implanted leads and then attempt to characterize the received signals as a particular cardiac event. Such cardiac events may include, for example, P waves, R waves, T waves, or arrhythmia events. By analyzing the type and timing of these cardiac events, the implantable device may determine whether therapy should be provided and, if so, the type of therapy to be provided (e.g., stimulation pulses).

For example, conventional heart pacemakers typically employ one or more intravascular leads that connect to a so-called "can" or a pacemaker housing containing a battery and associated electronic circuitry configured for pacing and sensing. Single-chamber pacemakers in the right atrium (RA) or right ventricle (RV) would typically be programmed in AAI or VVI modes, respectively, to inhibit pacing whenever intrinsic activity in that chamber is detected.

A dual-chamber pacemaker with RA and RV leads or a dual-chamber lead may have the ability to sense both atrial and ventricular electrical activity. For any patient with intermittent AV node conduction, it may be preferable to inhibit ventricular pacing and allow an intrinsic R wave to occur for a time after any P wave is detected on the RA lead. If ventricular pacing is needed, it is desirable to synchronize ventricular activity to atrial activity using an AV delay. The VDD programming mode has become common in dual-chamber pacemakers for patients with various degrees of AV block. Other common dual chamber modes include ODD and DDDR.

Current conventional implantable cardiac pacemakers include a housing and one or more electrically-conductive leads that connect to the housing through an electromechanical connection. The housing is implanted outside of the heart, such as in the pectoral region of the patient and contains controller electronics (e.g., a power source, microprocessor, capacitors, etc.) that provide pacemaker functionality. The leads traverse blood vessels between the housing and heart chambers in order to position one or more electrodes carried by the leads within the heart, thereby allowing the device electronics to electrically stimulate or pace cardiac tissue and measure or sense myocardial electrical activity.

To sense atrial cardiac signals and to provide a right atrial chamber stimulation therapy, the housing is conventionally coupled to an implantable right atrial lead including an atrial tip electrode that typically is implanted in the patient's right atrial appendage. The right atrial lead may also include an atrial ring electrode to allow bipolar stimulation or sensing in combination with the atrial tip electrode.

Before implantation of the pacemaker housing into a subcutaneous pocket of the patient, however, an external pacing and measuring device known as a pacing system analyzer (PSA) is used to ensure adequate lead placement, maintain basic cardiac functions, and evaluate pacing parameters for an initial programming of the device. In other words, a PSA is a system analyzer that is used to test how the leads would perform with an implantable device, such as an implantable pacemaker.

To sense right ventricular cardiac signals and provide ventricular stimulation therapy, the pacemaker housing is coupled to an implantable right ventricular lead including a right ventricular (RV) tip electrode and a right ventricular ring electrode. The lead for an implantable cardioverter defibrillator may also contain one or more electrodes for delivery of high-voltage therapy, such as a right ventricular coil electrode, a superior vena cava (SVC) coil electrode, or both. Typically, the right ventricular lead is transvenously inserted into the heart so as to place the right ventricular tip electrode in the right ventricular apex such that the RV coil electrode is positioned in the right ventricle and the SVC coil electrode is positioned in the right atrium and/or superior vena cava. Accordingly, the right ventricular lead can receive cardiac signals and deliver stimulation in the form of pacing and shock therapy to the right ventricle.

A cardiac rhythm management system may also deliver resynchronization therapy, in which electrical stimulation is delivered to coordinate the electromechanical activity of the chambers of the heart. Such system may use the leads placed in the right atrium and right ventricle along with an additional lead coupled to the pacemaker housing that extends through the coronary sinus to a distal tip electrode on the outer surface of the left ventricle. There may be one or more ring electrodes in electrical contact with the left ventricle, the left atrium or both. The tip electrode may reach a location in the venous vasculature of the left ventricle, including any portion of the coronary sinus, great cardiac vein, left marginal vein, left posterior ventricular vein, middle cardiac vein, and/or small cardiac vein, or any other cardiac vein accessible by the coronary sinus.

Accordingly, the coronary sinus lead may be designed for some or all of the following functions: receive atrial and/or ventricular cardiac signals; deliver left ventricular pacing therapy using a left ventricular tip electrode for unipolar configurations or in combination with at least one left ventricular ring electrode for bipolar configurations; deliver left atrial pacing therapy using at least one left atrial ring electrode; deliver high-voltage therapy using at least one coil electrode.

Although a portion of the leads is located within the heart, a substantial portion of the leads, as well as the pacemaker housing itself are outside of the patient's heart. Consequently, bacteria and the like may be introduced into the patient's heart through the leads, as well as the pacemaker housing, thereby increasing the risk of infection within the heart. Additionally, because the pacemaker housing is placed outside of the heart, the patient may be susceptible to Twiddler's syndrome, which is a condition caused by the shape and weight of the pacemaker housing itself. Twiddler's syndrome is typically characterized by subconscious, inadvertent, or deliberate rotation of the pacemaker housing within the subcutaneous pocket formed in the patient, hi one example, a lead may retract and begin to wrap around the pacemaker housing. Also, leads may dislodge from the endocardium or veins and cause the device to malfunction. Further, in another typical symptom of Twiddler's syndrome, the device may stimulate the diaphragm, vagus, or phrenic nerve, pectoral muscles, or brachial plexus. Overall, Twiddler's syndrome may result in sudden cardiac arrest due to conduction disturbances related to the device.

In addition to the foregoing complications, implanted leads may experience certain further complications such as incidences of venous stenosis or thrombosis, device-related endocarditis, lead perforation or disruption of the tricuspid valve and concomitant tricuspid insufficiency; and lacerations of the right atrium, right ventricle, coronary sinus, superior vena cava, and innominate vein or pulmonary embolization of electrode fragments during lead extraction.

To combat the foregoing limitations and complications, small sized devices configured for intra-cardiac implantation have been proposed. These devices, termed leadless pacemakers, are typically characterized by the following features; they are devoid of leads that pass out of the heart to another component, such as a pacemaker housing outside of the heart; they include electrodes that are affixed directly to the pacemaker housing of the device; the entire device is attached to the heart; and the device is capable of pacing and sensing in the chamber of the heart where it is implanted.

Leadless pacemaker devices that have been proposed thus far offer limited functional capability. These devices can sense electrical activity in one chamber and deliver pacing pulses in that same chamber, and thus offer single chamber functionality. For example, a leadless pacemaker device which is located in the right atrium would be limited to offering AAI mode functionality. An AAI mode leadless pacemaker can only sense electrical activity in the right atrium, pace in the right atrium and inhibit pacing function when an intrinsic event is detected in the right atrium within a preset time limit.

Similarly, a leadless pacemaker device that is located in the right ventricle would be limited to offering VVI mode functionality—see FIG. 1. Shown here is a conventional leadless pacemaker 10 implanted in the apex of the right ventricle using a helix screw 11, which also serves as an electrode. One or more other electrodes 12 may be used for sensing electrical activity in the right ventricle; wherein electrode 11 is used for pacing in the right ventricle or inhibiting pacing function when an intrinsic event is detected in the right ventricle within a preset time limit. To gain widespread acceptance by clinicians, it would be highly desirable for leadless pacemaker devices to have dual chamber pacing/sensing capability (VDD or ODD mode) along with other features, such as rate adaptive pacing.

It has been proposed to implant sets of multiple leadless pacemaker devices within a single patient, such as when one or more leadless pacemaker devices are located in the right atrium and one or more leadless pacemaker devices are also located in the right ventricle. The atrial leadless pacemaker devices and the ventricular leadless pacemaker devices may wirelessly communicate with one another to convey pacing and sensing information therebetween so as to coordinate pacing and sensing operations between various leadless pacemaker devices.

However, these sets of multiple leadless pacemaker devices experience various limitations. For example, if there is a wireless communication link between these devices, all devices must expend power to maintain the link. The wireless communication link should be maintained continuously in order to constantly convey pacing and sensing information between, for example, atrial pacemaker device(s) and ventricular pacemaker device(s). This exchange of pacing and sensing information is necessary to maintain continuous synchronous atrioventricular coordination.

Further, it is difficult to maintain a reliable wireless communications link between leadless pacemaker devices. The leadless pacemaker devices utilize low-power transceivers that are located in a constantly changing electrical environment within the associated heart chamber. The transmission characteristics of the environment surrounding a leadless pacemaker device change due in part to the continuous cyclical motion of the heart and change in blood volume. Hence, the potential exists that the communication link is broken or intermittent.

A further limitation of the existing cardiac leadless pacemakers is theft limited life span, which is typically less than about 5 years. This limitation is a result of having to use a very small battery so as to minimize the overall size of the device and facilitate its minimally invasive implantation techniques. The need exists to configure a leadless pacemaker in such as way as to extend its useful life, for example by providing a longer lasting battery, allowing for a battery recharge or battery replacement when it is depleted.

To overcome the issues of sensing and pacing in multiple chambers of the heart, my previously filed '653 patent application proposes to implant a plurality of electrodes in the triangle of Koch, His bundle and surrounding areas. This location is unique in the cardiac conduction system of the heart in that it may allow pacing multiple heart chambers from a single location in accordance with my '653 application. Since the exact location of specific conduction pathways is not always easy to find based on geometrical and anatomical variations between patients, a plurality of electrodes may be used to cover the entire area of the interest with locations where electrical activity may be probed. Subsequent selection process may be used to identify the best electrodes suitable for sensing and pacing one or more cardiac chambers depending on the particular anomaly of rhythm for a specific patient. While proposed approach is generally useful, it mostly described the use of conventional pacemaker technology connected to the heart by a single conduit containing a plurality of leads. Given the limitations of the pacemaker technology described above, it may be more desirable to adapt leadless pacemaker technology for use with this approach, namely cardiac pacing via triangle of Koch and His bundle.

The need therefore exists for a single long-lasting leadless pacemaker device capable of sensing and pacing one or more chambers of the heart from a single location, such as triangle of Koch and His bundle and closely surrounding areas of the heart.

SUMMARY OF THE INVENTION

Accordingly, it is an object of the present invention to overcome these and other drawbacks of the prior art by providing a novel multi-electrode leadless pacemaker and methods of using thereof aimed at providing heart stimulation for one or more heart chambers from a single intra-cardiac location.

It is another object of the present invention to provide a multi-electrode cardiac pacemaker adapter configured to use a conventional single-electrode leadless pacemaker for producing cardiac pacing of His bundle with multiple electrodes as a therapy for pacing one or more multiple cardiac chambers at the same time.

It is a further object of the present invention to provide an adapter for converting a conventional cardiac pacemaker for use with an implantable multi-electrode assembly.

It is yet a further object of the present invention to provide the leadless cardiac pacemaker configured for stimulation of the heart in the area of triangle of Koch and His bundle.

The leadless cardiac pacemaker of the invention generally comprises a housing configured to be implanted entirely within a single heart chamber at a predetermined target area, such as triangle of Koch, His bundle and surrounding nearby areas. The leadless pacemaker also comprises a plurality of individual electrodes located on or extending from the housing and configured for delivering electrical stimuli to a cardiac tissue at the target area implantation site. At least some of the plurality of individual electrodes may be further configured to sense electrical activity of said cardiac tissue at the target area, such as sensing right atrial electrical activity for example.

The leadless cardiac pacemaker of the invention further comprises a controller hermetically sealed within the housing. The controller may be configured to operate in one of the following two modes following implantation of the leadless cardiac pacemaker:
  an individual electrodes evaluation mode, wherein the controller is operated to interrogate the individual electrodes individually or in groups to determine a subset thereof meeting a predetermined criteria, and
  a therapeutic mode, wherein the controller is operated to deliver the electrical stimuli to the cardiac tissue at the target area.

Implantation of the plurality of individual electrodes is intended to cover the area of triangle of Koch and His bundle. At least some individual electrodes are expected to hit the His bundle conduction pathways. Other individual electrodes may be located near His bundle conduction pathways but not be electrically coupled thereto. Electrical evaluation of those electrodes that are electrically coupled to His bundle may be used to identify at least one or more electrodes suitable for subsequent ventricular pacing using at least one predetermined criteria, such as for example a best capture threshold. Evaluation of those electrodes that are positioned to not be electrically coupled to His bundle may be used to identify one or more individual electrodes suitable for subsequent atrial pacing and/or sensing of atrial electrical activity. Remaining individual electrodes may be abandoned.

Depending on the condition of the subject, using selected subset of individual electrodes may allow providing of cardiac pacing of multiple cardiac chambers (such as direct atrial pacing and ventricular pacing via stimulation of His bundle) from a single intra-cardiac location with a single implantable cardiac pacemaker. The present invention therefore allows to avoid a need to implant multiple leadless cardiac pacemakers and coordinate their pacing activities when more than one cardiac chamber is in need of a dedicated rhythm management therapy.

The present invention further describes an adapter for delivering rhythm management electrical stimuli to one or multiple heart chambers using a conventional cardiac pacemaker. The adapter in this case may include a housing configured to be implanted entirely within a single heart chamber at a predetermined target area. The housing may be also configured to operably connect to the conventional cardiac pacemaker and retain thereof at the implantation site.

The adapter may further include a plurality of individual electrodes located on or extending from the housing and configured for delivering electrical stimuli to a cardiac tissue at target area of implantation site such as His bundle or triangle of Koch. At least some of the plurality of individual electrodes may be further configured or used to sense electrical activity of local cardiac tissue at the target area.

The adapter may further include an electronic switch hermetically sealed within the housing and configured to deliver atrium pacing stimuli generated by the conventional cardiac pacemaker to at least one of the individual electrodes selected for atrial pacing. The electronic switch may be further configured to deliver ventricular pacing stimuli from the conventional cardiac pacemaker to at least one other individual electrodes selected for ventricular pacing via stimulation of His bundle, whereby said multiple heart chambers may be paced from a single intra-cardiac location.

The electronic switch may be also configured for operating to select a subset of the individual electrodes using best capture threshold criteria, while the leadless conventional cardiac pacemaker may be configured to deliver electrical stimuli to triangle of Koch or His bundle for ventricular pacing purposes when atrial pacing or sensing of atrial electrical activity is not needed, such as for example in case of permanent atrial fibrillation.

The present invention also describes a method for providing cardiac rhythm management therapy comprising the following steps:
  a. providing a leadless cardiac pacemaker comprising a housing configured to be implanted entirely within a single heart chamber, a plurality of individual electrodes located on or extending from the housing, and a controller located within the housing and operably connected with the individual electrodes,
  b. implanting the leadless cardiac pacemaker at a target area defined by triangle of Koch, His bundle and surrounding areas while positioning the individual electrodes throughout said target area,
  c. evaluating the plurality of individual electrodes using a predetermined criteria to select at least one individual electrode suitable for atrial pacing, and at least one other individual electrode suitable for ventricular pacing via delivering of electrical stimuli to His bundle, and d. operating the controller to deliver atrial pacing and ventricular pacing via the respective selected individual electrodes from a single intra-cardiac location.

A variety of tissue fixation elements and corresponding implantation techniques specific to the target area of interest is described below in greater detail.

BRIEF DESCRIPTION OF THE DRAWINGS

The subject matter is particularly pointed out and distinctly claimed in the concluding portion of the specification. The foregoing and other features of the present disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through the use of the accompanying drawings, in which:

DETAILED DESCRIPTION OF THE PREFERRED EMBODIMENT OF THE INVENTION

Figure 1:
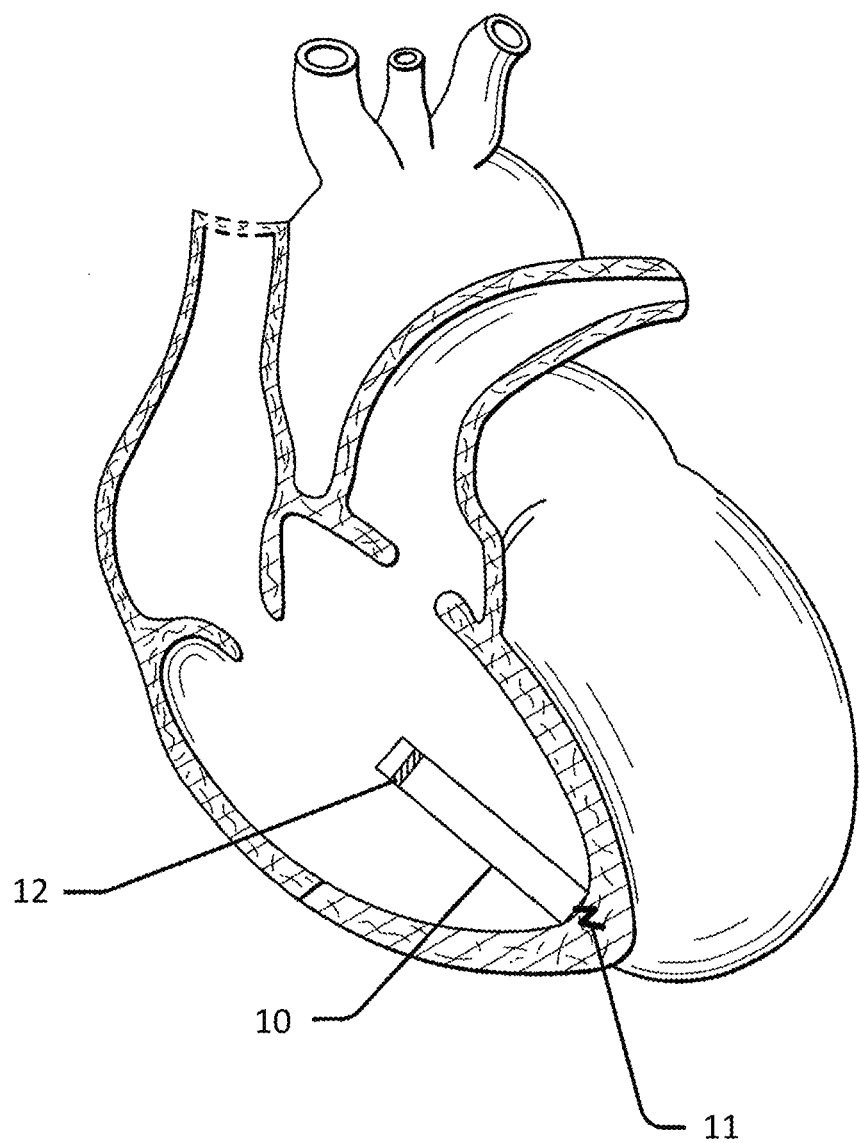
FIG. 1 is a cross-sectional view of a prior art conventional leadless pacemaker positioned in the right ventricle of the heart.

The following description sets forth various examples along with specific details to provide a thorough understanding of claimed subject matter. It will be understood by those skilled in the art, however, that claimed subject matter may be practiced without one or more of the specific details disclosed herein. Further, in some circumstances, well-known methods, procedures, systems, components and/or circuits have not been described in detail in order to avoid unnecessarily obscuring claimed subject matter. In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and make part of this disclosure.

Figure 2:
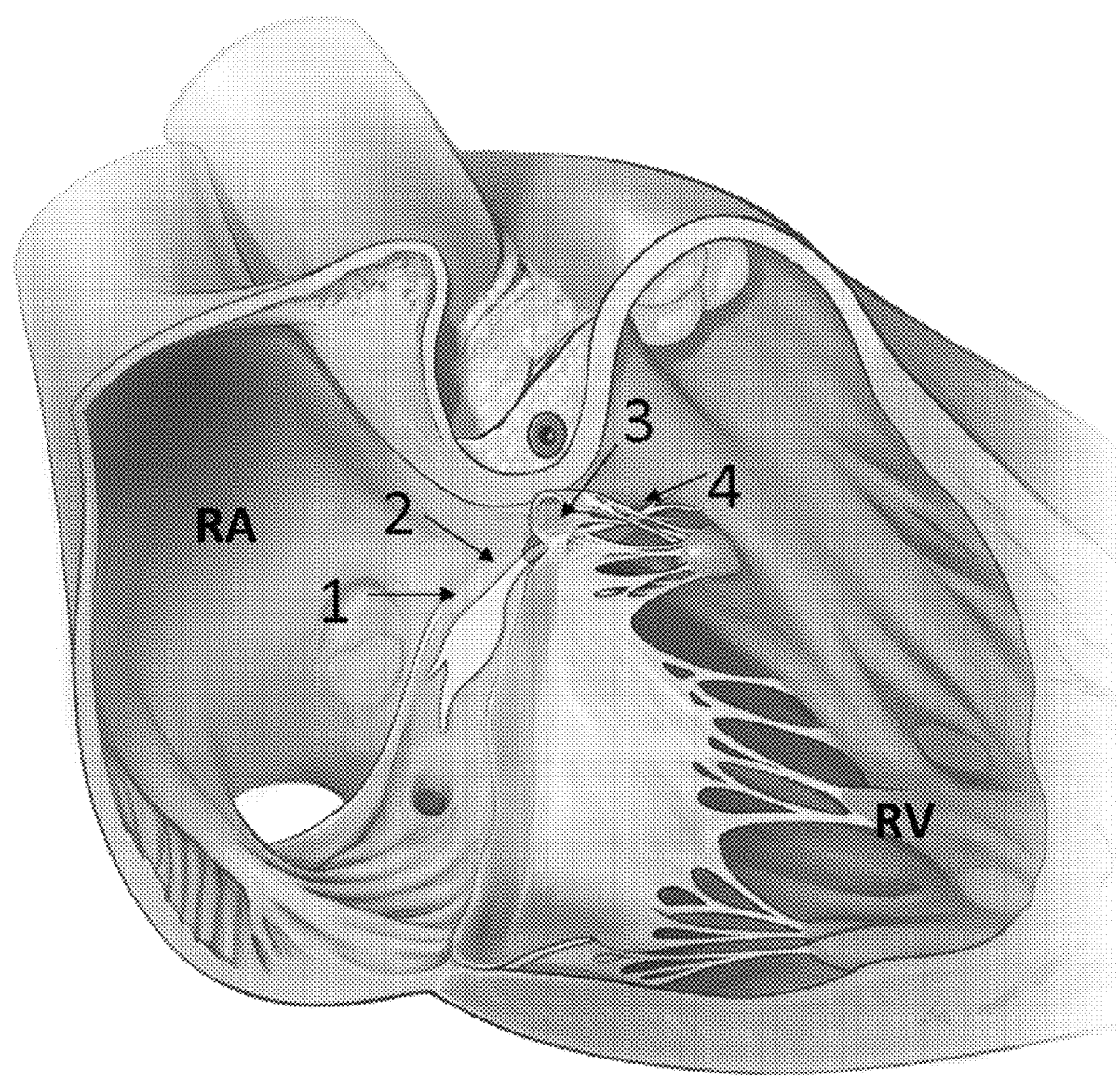
FIG. 2 is a cut-out view of various chambers of the heart.
Figure 3:
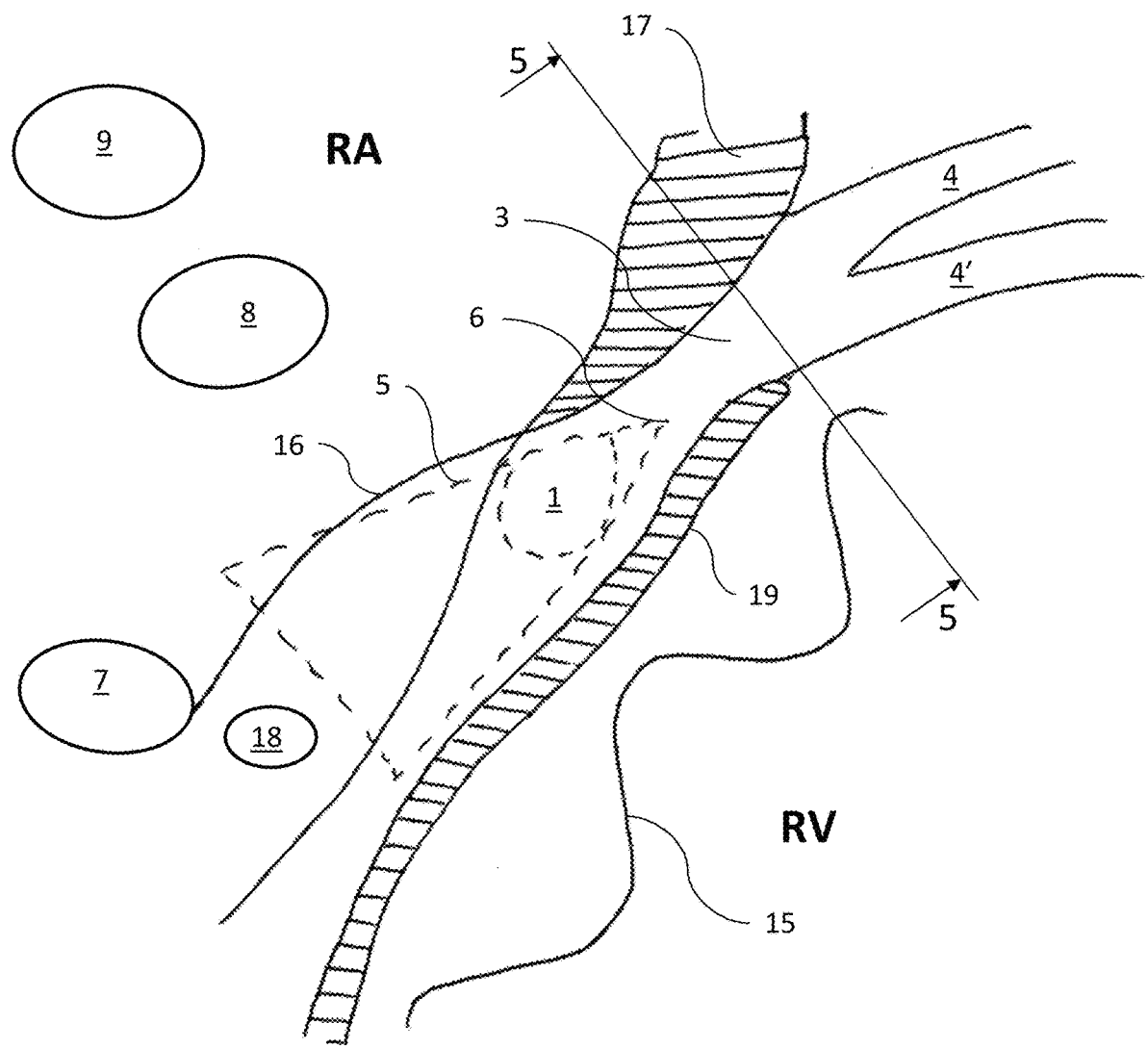
FIG. 3 is a schematically-drawn close-up of the triangle of Koch and His bundle.

Referring now to a general cut-out view of FIG. 2 and a close-up shown in FIG. 3, compact AV node 1 in the right atrium (RA) converges into a transitional zone 2 broadly including the triangle of Koch 5 before continuing as the His bundle 3 at the apex 6 of the triangle of Koch 5. The His bundle 3 penetrates the membranous septum and continues as left 4 and right 4' bundle branches on the summit of the muscular septum. Also shown are inferior vena cava 7, foramen ovale 8, superior vena cava 9, tricuspid valve annulus 19 and leaflet 15, tendon of Todaro 16, central fibrous body 17, and coronary sinus 18.

Figure 4:
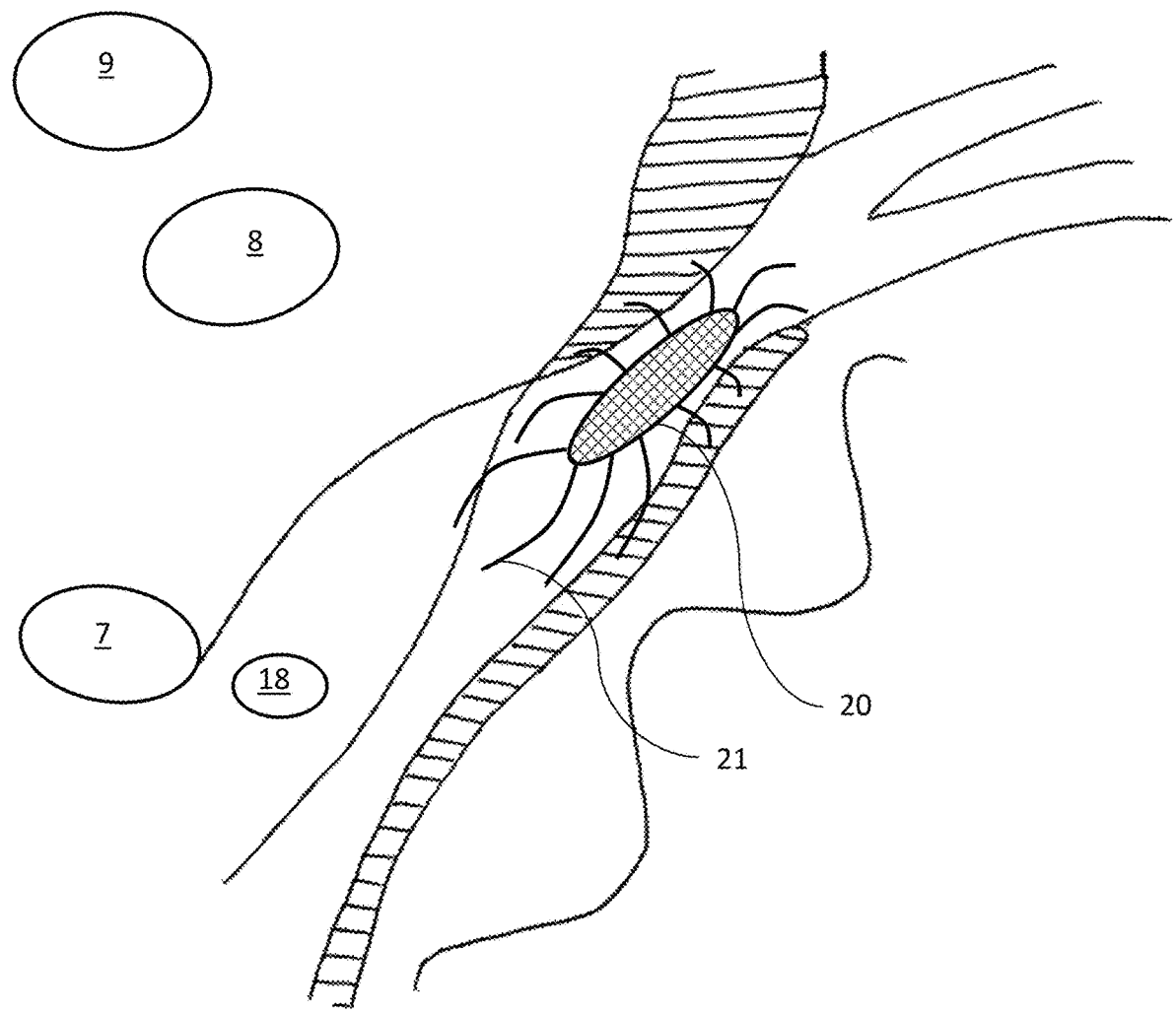
FIG. 4 illustrates a top view of a general location for positioning the multi-electrode leadless pacemaker of the invention in the area of triangle of Koch and His bundle.
Figure 5:
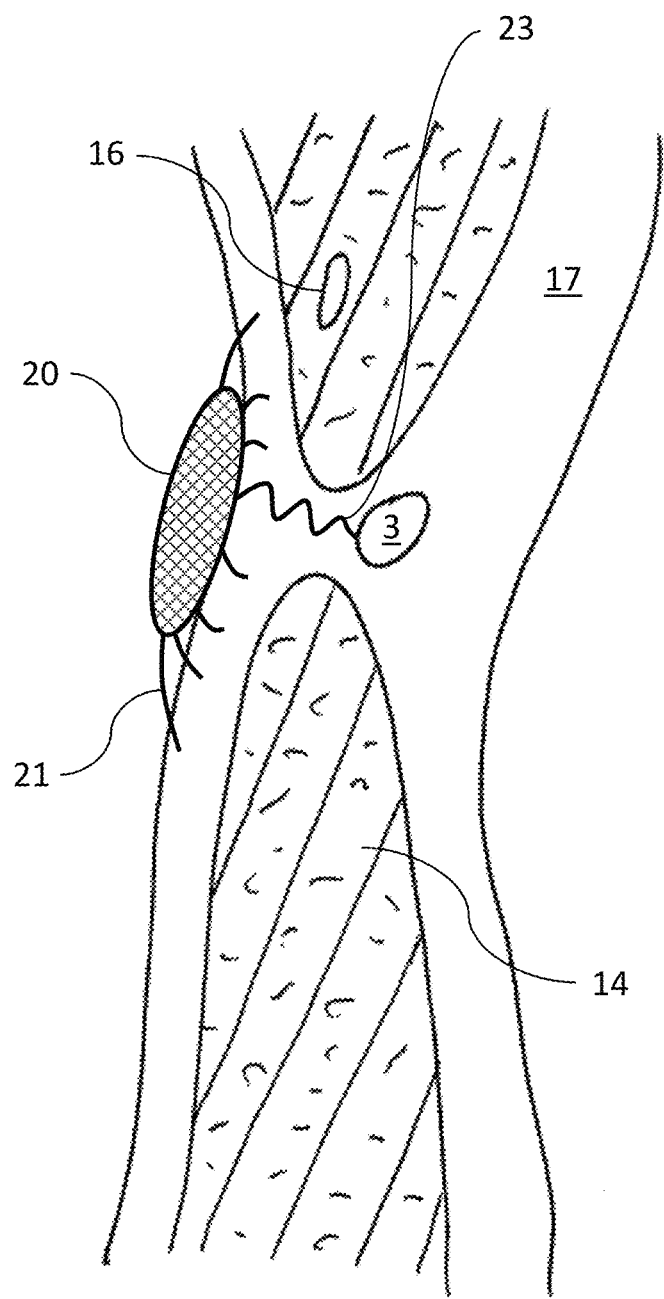
FIG. 5 illustrates a sagittal cross-sectional view of the same as in FIG. 4.

According to the present invention, one general location for the leadless pacemaker 20 may be anchored in the target area of the apex of the triangle of Koch transitioning to His bundle—as seen in FIG. 4 and FIG. 5. Multiple electrically separated individual electrodes 21 may be located throughout this location and closely surrounding areas. At least two, at least three, at least four, at least five or more of individual electrodes 21 may be provided. In embodiments, any number of individual electrodes between 2 and 16 may be provided. The number of individual electrodes can be 2, 3, 4, 5, 6, 7, 8, 9, 10, 11, 12, 13, 14, 15, or 16 electrodes. Individual electrodes 21 may or may not be arranged in a linear fashion upon their placement. In embodiments, individual electrodes 21 may or may not be located along one or a few implantable leads so as a single lead contains more than one individual electrode 21 as the invention is not limited in this regard. The device of the invention may be configured to allow individual electrodes to be placed to cover at least a large two-dimensional portion or the entire 2D surface of the target area as described herein. At least some or all of the electrodes 21 may be individually positioned at desired locations at the target area independently of other individual electrodes 21.

This target area is advantageous for locating the leadless pacemaker 20 because among other reasons it allows probing, evaluation, sensing and corresponding pacing of one or more chambers of the heart from a single intra-cardiac location.

A general design for the leadless pacemaker 20 comprises electronic pacemaker controller that is substantially enclosed in a hermetic housing suitable for placement on or attachment to the inside or outside of a single cardiac chamber. The pacemaker may have a plurality of individual electrodes located on or near the housing, for delivering pacing pulses or other electrical stimuli to the muscle of the cardiac chamber and optionally for sensing electrical activity of the heart. The housing may contain a primary battery and suitable electronic circuitry to provide power and control for pacing, sensing, and communication according to programmed instructions, for example bidirectional communication (in particular by using an antenna or a telemetry coil) with at least one other device within or outside the body, such as an external programmer. The housing may optionally contain controller circuits for sensing cardiac activity from the electrodes. The housing may further optionally contain controller circuits for monitoring its own status and operational parameters. The housing may also contain circuits for controlling these operations in a predetermined manner.

Some exemplary embodiments of the controller may be configured to provide communication between the implanted leadless pacemaker pulse generator and a device internal or external to the body, with power requirements similar to those for cardiac pacing, to enable optimization of battery performance. In an illustrative embodiment, an outgoing telemetry can be adapted to use no additional energy other than the energy contained in the pacing pulse, although the invention is not limited in this regard.

A power supply may be hermetically contained within the housing of the leadless pacemaker 20 and coupled to the internal pulse generator of the device controller. The power supply may supply all energy for operations and electrical pulse generation as a source internal to the housing. In the illustrative embodiment, the power supply may include a primary battery with an energy density of at least 2 watt-hours/cubic centimeter (W·h/cc).

In various embodiments, the electrodes 21 may be formed on the housing, integrally to the housing of the pacemaker 20 or may extend from the housing and coupled there while separated by a distance, for example up to 2 cm, from the housing as is typical for a screw-in electrode.

The controller may be configured to communicate with a device external to the leadless pacemaker 20, for example typically an external programmer or another implanted device, by using communication signals transmitted wirelessly. Communication is typically bidirectional although some implementations may include only one-way communication, either to or from the leadless pacemaker 20. Implantable systems of the invention may be configured to communicate to an outside device via long distance radiofrequency (RF) schemes, for example, Medical Implant Communication Service (MICS) transceivers, and other RF or inductive telemetry schemes. The controller may control electrical stimuli delivery based on one or more programmable parameters and can be programmed by wirelessly transmitted communication signals.

The illustrative power supply may also be a primary battery including a beta-voltaic converter that obtains electrical energy from radioactivity. In some embodiments, the power supply can be selected as a primary battery that has a volume less than approximately 1 cubic centimeter. Yet, in further embodiments, the power supply may be a rechargeable battery, in which case an additional energy conversion element may be provided within the housing of the pacemaker to facilitate power transmission and conversion of energy in order to recharge the main battery of the device. One example of such power conversion is a device configured to convert high intensity focused ultrasound (HIFU) waves which may be supplied from an external single or a plurality of ultrasound transducers and focused on a location of the leadless pacemaker of the invention—in which case the incoming ultrasound energy may be converted by a piezoelectric transducer into electrical power suitable for recharging of a device battery from time to time, such as explained for example in the U.S. Pat. No. 8,649,875 incorporated herein in its entirety by reference.

In an illustrative embodiment, the primary battery may be selected to source no more than 70 microwatts instantaneously since a higher consumption may cause the voltage across the battery terminals to collapse. Accordingly, in one illustrative embodiment, the circuits of the leadless pacemaker may be designed to consume no more than a total of about 65 microwatts. The design may in some instances avoid usage of a large filtering capacitor for the power supply or other accumulators such as a supercapacitor or rechargeable secondary cell to supply peak power exceeding the maximum instantaneous power capability of the battery, components that would add volume and cost.

In various embodiments, the system can manage power consumption to draw limited power from the battery, thereby reducing device volume. Each circuit in the system can be designed to avoid large peak currents. For example, cardiac pacing can be achieved by discharging a tank capacitor (not shown) across the pacing individual electrodes 21. Recharging of the tank capacitor is typically controlled by a charge pump circuit. In a particular embodiment, the charge pump circuit may be throttled to recharge the tank capacitor at constant power from the battery.

Specific placement and subsequent usage of individual electrodes 21 may be arranged based on a detailed description contained in my '653 application. Briefly, all individual electrodes 21 may be first implanted and permanently placed in the target area of triangle of Koch so that at least some of them may be electrically coupled with the conduction pathways located in cardiac tissue of His bundle and surrounding areas. Initial interrogation of some or all of the individual electrodes 21 may be conducted to determine their suitability for subsequent pacing of the specific heart chambers depending on a particular condition of the subject. Even though individual electrodes 21 are all located near each other, at least some of the individual electrodes may be implanted at locations directly suitable for stimulation of His bundle and therefore for ventricular pacing, while other nearby individual electrodes 21 may be located at the atrial cardiac tissue not suitable for His bundle pacing but still amenable for delivering atrial stimulation pulses.

The controller of the leadless pacemaker may be configured for operating in the individual electrode evaluation mode to select at least one or more individual electrodes suitable for atrial pacing and, at the same time, select at least one or more other individual electrodes suitable for ventricular pacing via delivering of electrical stimuli to His bundle.

In embodiments, to evaluate individual electrodes 21, one electrode at a time may be activated in a unipolar or bi-polar mode with various levels of pacing voltage so as to determine whether its particular location and performance is adequate for desired cardiac pacing purposes. Evaluation of all individual electrodes 21 may be conducted using one electrode at a time or pairing electrodes with each other.

Individual electrodes 21 may then be ranked as to their suitability based on one or more predetermined criteria. Examples of the predetermined criteria for selecting a subset of individual electrodes may include (i) appearance of an acceptable paced P-wave on an ECG tracing when the cardiac pacing is desired to correct an atrial arrhythmia, (ii) selective capture of the bundle of His and/or triangle of Koch, (iii) non-selective capture of the bundle of His and/or triangle of Koch, (iv) appearance of an acceptable QRS complex on an ECG tracing when the cardiac pacing is desired to correct a ventricular arrhythmia. Once the initial selection is made, an addition sub-selection of the most suitable subset of selected individual electrodes 21 may be conducted so as to determine the best individual electrodes or pairs of individual electrodes 21 suitable for subsequent pacing purposes with the lowest effective voltage thresholds.

Subject-specific cardiac stimulation may then commence using the subset of individual electrodes 21 selected based on their highest ranking. The controller may be switched to operate in the therapeutic mode, in which the controller may function to deliver electrical stimuli suitable for atrial pacing using one or a group of selected individual electrodes 21 and, at the same time, deliver other electrical stimuli suitable for ventricular pacing via stimulation of His bundle using another one or several individual electrodes 21. At least one, at least two, at least three or more individual electrodes 21 may be used for active cardiac pacing after the selection process is complete. Non-selected one or more individual electrodes 21 may be abandoned or used for sensing or other supplemental purposes. The entire electrode selection process may be repeated from time to time if the subject condition changes or for other reasons, whereby previously dormant electrodes may be re-activated and used for cardiac pacing purposes if their suitability ranking increases and exceeds other individual electrodes 21. The present invention therefore provides for a uniquely advantageous opportunity to deliver suitable individualized atrial and ventricular cardiac pacing via respective individual electrodes 21 (after their initial evaluation) from a single intra-cardiac location using a single implantable device.

In embodiments, individual electrodes 21 may be secured in place and achieve close electrical coupling to the cardiac tissue using a variety of known securement methods, including being held in close contact with the surface of the cardiac tissue, being implanted under the surface of the cardiac tissue, being fused with the cardiac tissue, or by other known methods. In embodiments, one or more electrodes may be equipped with a helical cork-screw—type distal end and configured to be turned so as to bury themselves into the layers of cardiac tissue underneath thereof. As described later, all, some, or one-at-a-time placement of individual electrodes 21 may be used prior to, during, or after the implantation of the leadless pacemaker 20 so as to achieve their placement into the target area of the heart.

In one exemplary embodiment seen in FIGS. 4 and 5, the leadless pacemaker 20 may be implanted and secured in position by a fixation screw electrode 23 to connect thereof electrically to His bundle 3. For the purposes of this invention, the term "fixation screw" is used to include other similar fixation approaches such as one or more self-activated spring-loaded or shape-memory staple, claw, hook and others that generally act by clamping onto or embedding themselves into nearby cardiac tissue once released from their captive straight position.

Since the His bundle is a structure located deep within the myocardium, the positioning of the individual electrodes 21 may be optimized in three dimensions. Typically, the His bundle is reached from the atrium by mapping in the area of the triangle of Koch. The correct region at which the endocardium should be penetrated with the individual electrodes 21 to reach the His bundle may be identified at least on a preliminary basis by finding the spot where the largest His bundle potential is measured. The fixation screw may then be placed in this spot.

Previously published studies have revealed that both the capture threshold and the sense thresholds as well as the ability to distinguish the signal from the His bundle with the implantable electrodes may be dependent on the depth of the individual electrode in the tissue, see, for example, Deshmukh et al., Circulation 2000; 101; 869-877 and Laske et al., PACE 2006; 29; 397-405. With a conventional fixation screw, which has a length of the helix of approximately 1.5-2.0 mm, the helix may in some cases never reach the optimal depth. In order to reach the desired spot in close proximity to the bundle of His, a longer fixation screw may be required. This has been studied in Karpawich et al., PACE, Part H, 1992; 15; 2011-2015, where a helix screw having a length of 4.5 mm was used to pace His bundle. Useful examples of suitable fixation screws are found in U.S. Pat. No. 7,177,704, which describes a helically shaped electrode partially masked with an insulative material, leaving an intermediate area unmasked and electrically conductive to allow for pacing at specific depths within the heart tissue. Another suitable fixation approach configured for operating at the His bundle location is found in U.S. Pat. App. No. 20100318147.

Other individual electrodes 21 may be positioned throughout surrounding areas of triangle of Koch and may penetrate at same or different depths into the myocardium 14 at least in some locations. In embodiments, electrodes 21 may be made using electrically conductive single- or multi-strand wires or other electrical conduits. Some or all electrodes 21 may be made to have electrical insulation along a part or their entire depth. In further embodiments, some or all electrodes 21 may be made to be flexible, ranging in stiffness from flaccid to more rigid, such as for example pre-shaped and spring-like, whereby their location and shape as related to the housing of the leadless pacemaker 20 may be predetermined.

While the details of implantation techniques and methods with regard to individual embodiments will be described in greater detail below, the following is a description of a general implantation approach suitable for many of the leadless pacemaker embodiments of the present invention. Broadly speaking, the leadless pacemaker of the invention may be implanted using a surgical implantation approach or a minimally invasive implantation approach, which is, of course, a preferred implantation approach to minimize trauma to the subject. Surgical approach may still be used in certain circumstances, such as when the subject's vasculature is compromised and is not suitable for traversing therethrough of the leadless pacemaker delivery system. Another opportunity for surgical implantation may be when a heart surgery results in a need for a cardiac pacemaker at the end thereof. Surgical approach may also be used in animal experiments so as to speed up the implantation technique and assure accurate placement of the individual electrodes under direct vision guidance. When a surgical implantation technique is used, simple direct suturing or stapling of the leadless pacemaker to the exposed target cardiac tissue may be used to secure the device in place. As an alternative to suturing, a gluing operation or another fusing between the pacemaker and the cardiac tissue may be accomplished as the invention is not limited in this regard. In further embodiments, the positioning of the pacemaker under a tissue flap which may be optionally closed with a suture or a staple may also be used to secure the device in place.

Minimally invasive or percutaneous delivery of the leadless pacemaker of the invention may be accomplished using conventional leadless pacemaker delivery approaches, with some modifications for specific embodiments as described later. In general, a minimally invasive or a percutaneous entry to a major blood vessel may be first established and a suitably sized catheter may be threaded towards the right atrium of the heart. While in most cases, a femoral vein approach may be used so the delivery catheter reaches the right atrium from the lower vena cava 7, upper vasculature may also be used, in this case the delivery catheter may be inserted through a left subclavian vein for example and reach the right atrium from the superior vena cava 9.

In embodiments, the distal end of the delivery catheter may be positioned over the target area as described above, followed by the deployment of the leadless pacemaker of the invention along with its individual electrodes and securement thereof in place using for example at least one securement screw, which in some cases may also be used as one of the individual electrodes of the leadless pacemaker. As an alternative to a fixation screw, some or all of the embodiments may also feature one or more shape-memory hook or claw configured to form a loop and grasp onto nearby cardiac tissue when released from their captive initially-straight configuration.

Pacemaker implantation procedure may be aided by using one or more visualization modalities such as ultrasound, X-Ray, fluoroscopy, CT, MRI, TEE or others, such as known in the field as the invention is not limited in this regard.

Evaluation of individual electrodes may be conducted following the implantation of the leadless pacemaker as described above, which in turn may be followed by selecting of the most suitable electrodes and activating the rhythm management functionality of the pacemaker.

Following initial implantation, the leadless pacemaker and its individual electrodes are expected to be encapsulated at their location over time. To facilitate retrieval and replacement, at least some embodiments of the invention may feature engagement elements such as loops extending from the main housing of the device. Once access to the device is established, these engagement features may be used to rotate the fixation screw in the direction opposite the one used during device placement so as to retrieve the fixation screw from cardiac tissue. A retrieval system may be further used in this case to gain a minimally invasive access and secure connection to the device. Once such a connection is established, the pacemaker may be dislodged from its location and retrieved if needed.

Subject-Specific Configurations of the Leadless Pacemaker

Figure 6:
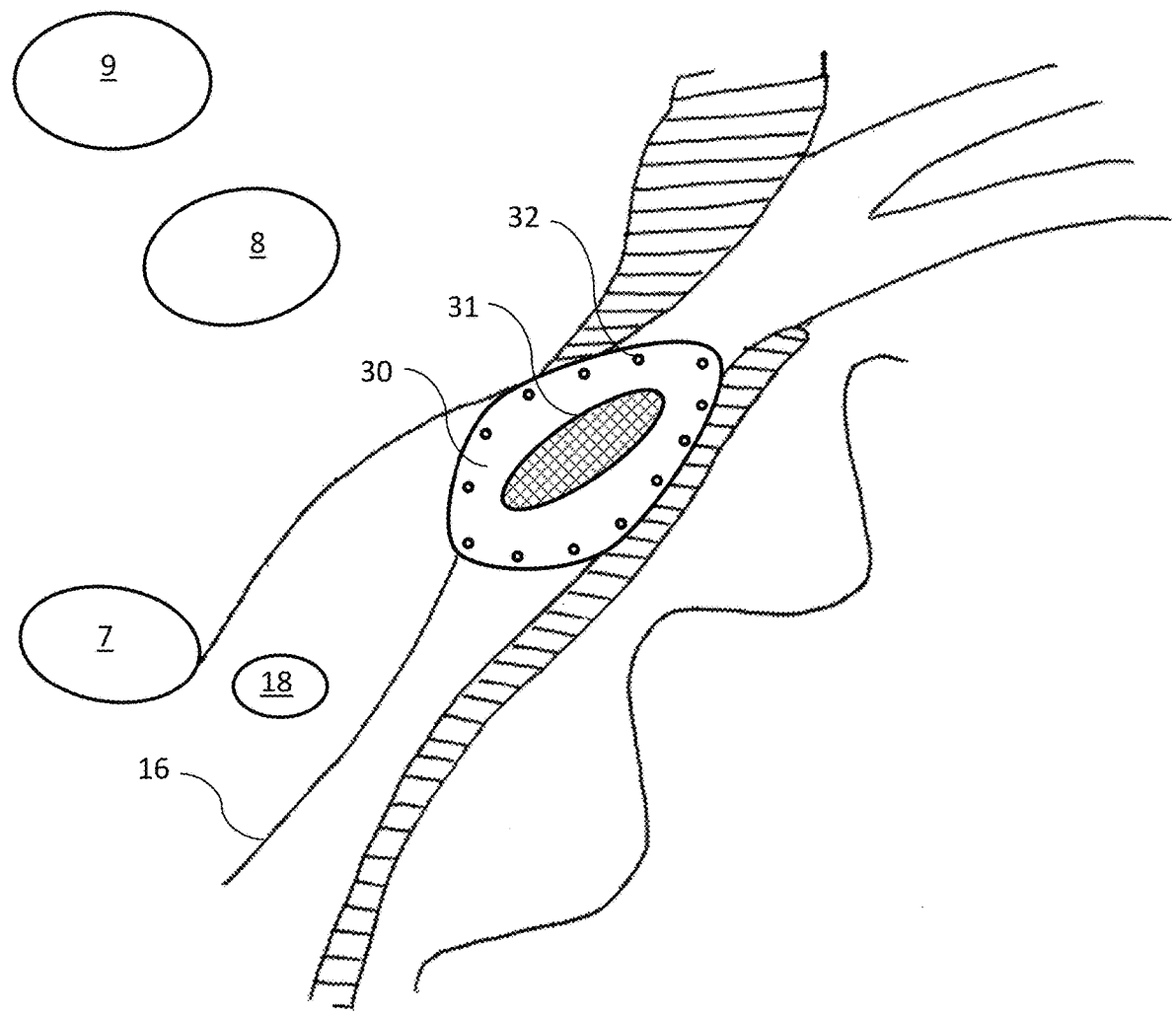
FIG. 6 shows a top view of a general position of an alternative configuration of the multi-electrode leadless pacemaker in the area of triangle of Koch and His bundle.
Figure 7:
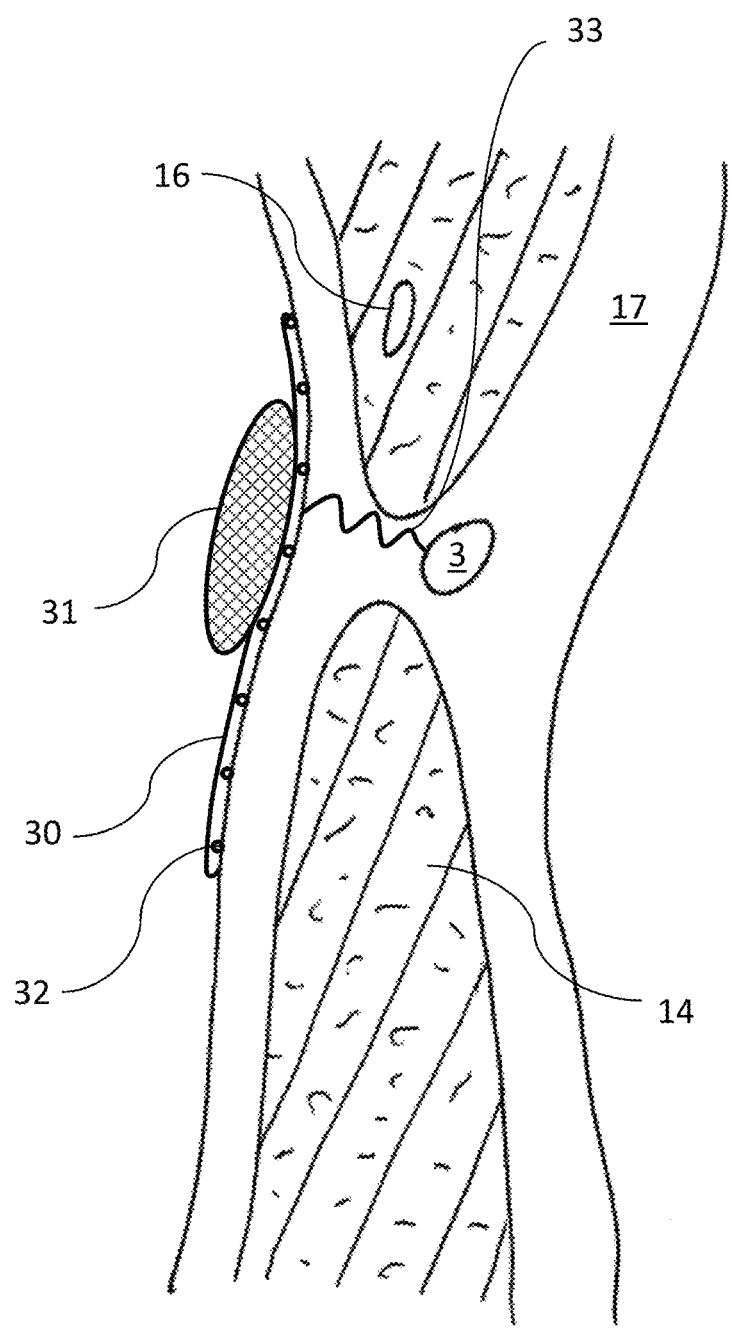
FIG. 7 shows a cross-sectional side view of the same as in FIG. 6.

FIGS. 6 and 7 illustrate a further embodiment of the invention in which individual electrodes 32 and the main pacemaker housing 31 may be embedded in an elastic flexible member 30. Individual electrodes 32 may be encapsulated in the flexible member 30 in such a way that when the flexible member 30 is placed at the target implantation zone, the electrodes 32 are in close contact with the cardiac tissue, whereby assuring electrical conductance thereto from the main housing 31, see FIGS. 9 and 10. Individual electrodes 32 may be positioned along the periphery or throughout the surface of the flexible member exposed to the cardiac tissue.

The flexible member 30 may be made in a general shape of a thin disk using an elastic biocompatible and biostable material such as a polyurethane, a silicone, or a mix thereof. One or more standard sizes and shapes of the flexible member 30 may be provided such as for example between 1 and 6 sizes, such as 1 size, 2 sizes, 3 sizes, 4 sizes, 5 sizes, 6 sizes or even more if necessary as the invention is not limited in this regard. Each size and shape may be selected based on a predetermined range of lengths, widths and 3D shapes of the target area for implantation of the device as described above—as recorded for a large enough number of subjects to be representative of the general population. Accurate cardiac imaging techniques may be used for this purpose as mentioned elsewhere in this specification, primarily cardiac MRI or CT imaging.

In embodiments, the flexible member 30 may have a round disk shape, an oval disk shape, a pear-shaped disk, a generally triangular shaped disk repeating the geometry of triangle of Koch and extending into His bundle, or any other suitable shape. A general length dimension may be selected to be about 20 to 40 mm long, such as 20, 25, 30, 35, 40 mm or any length in between. A general width dimension may be selected to be about 15-35 mm, such as 15, 20, 25, 30, 35 mm or any width in between. In embodiments, an exemplary shape of the flexible member 30 may be a 25×35 mm oval with a thickness ranging from about 0.5 mm to 6 mm, such as 0.5 mm, 1 mm, 2 mm, 3 mm, 4 mm, 5 mm, 6 mm or any thickness in between.

Figure 9:
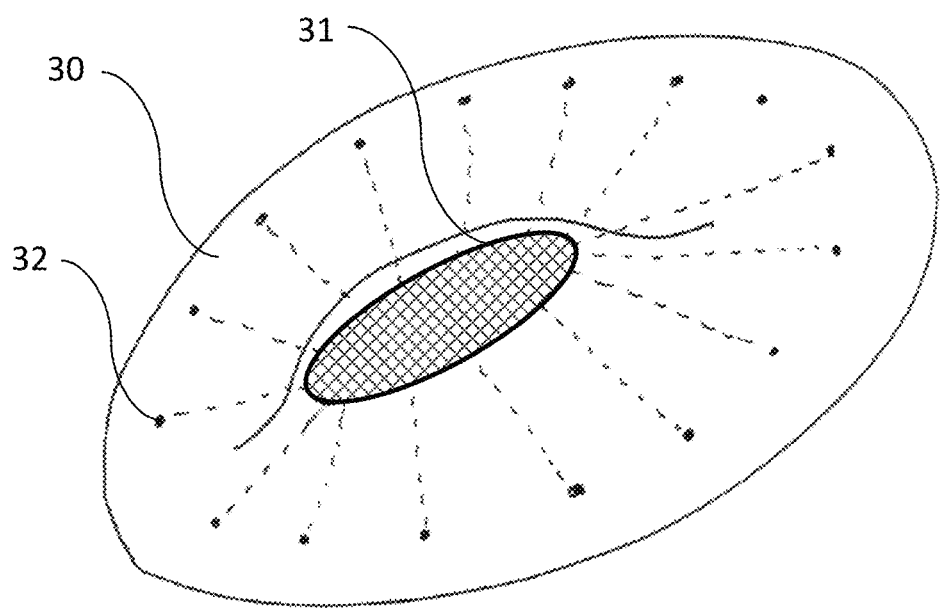
FIG. 9 is a top perspective view of yet another configuration of the leadless pacemaker of the present invention.

Individual electrodes 32 may include flexible leads made for example from a small diameter single wire or a multi-strand wire, such wires may be encapsulated in or attached to the body of the flexible member 30, see FIG. 9. Locations of distal tips of individual electrodes 32 may be selected to assure adequate coverage of the target area of the heart despite possible small deviations of positioning the leadless pacemaker of the invention from the intended location.

One advantage of this embodiment is in the ease of implantation of the device with all individual electrodes having a predetermined and fixed position with regard to the main housing 31. Since the flexible member 30 may bend easily, a delivery system may take advantage of the folding of the periphery or "wings" of the flexible member 30 around the main housing 31 so as to position the device in its folded state inside the delivery catheter configured for minimally invasive implantation. After positioning the flexible member 30 at the target area in the heart, it may be secured to remain at the site by using a fixation screw 33 or by other suitable means, see FIG. 7.

A further advantage of this configuration is that the shape of the flexible member 30 may be adjusted and trimmed to the size and shape most suitable for an individual subject. In embodiments, the original shape of the flexible member 30 and locations of individual electrodes 32 may be selected to assure that subject-specific trimming of the outer portions of the flexible member 30 would not disturb or damage any of the individual electrodes 32. In other embodiments, however, at least some of the individual electrodes 32 may be deliberately located in areas of the flexible member 30 which may be trimmed off prior to implantation so as to allow the physician to have flexibility as to the location of remaining electrodes on the trimmed flexible member 30. This configuration may be advantageous for example in situations where cardiac rhythm management is done via excitation of groups of electrodes rather than each individual electrode one at a time.

A further yet advantage of this embodiment is that the ability to trim the device to an individual size and shape may help in reducing the number of device sizes that may be required to treat a broad range of subjects, with subsequent advantages in device procurement, logistics and stocking for a hospital.

In other embodiments, the flexible member 30 may also be made to size to match the target area geometry by (i) obtaining a detailed 3D image of the target area using any suitable imaging techniques such as MRI, CT, fluoroscopy, transesophageal echo (TEE), other ultrasound imaging, etc. and (ii) producing a custom-shaped flexible member 30 by using a custom mold or by using 3D printing techniques. In embodiments, a subject-specific flexible member 30 may be produced to incorporate some or all individual electrodes 32 and have provisions to either retain or connect to the main housing 31.

Figure 8:
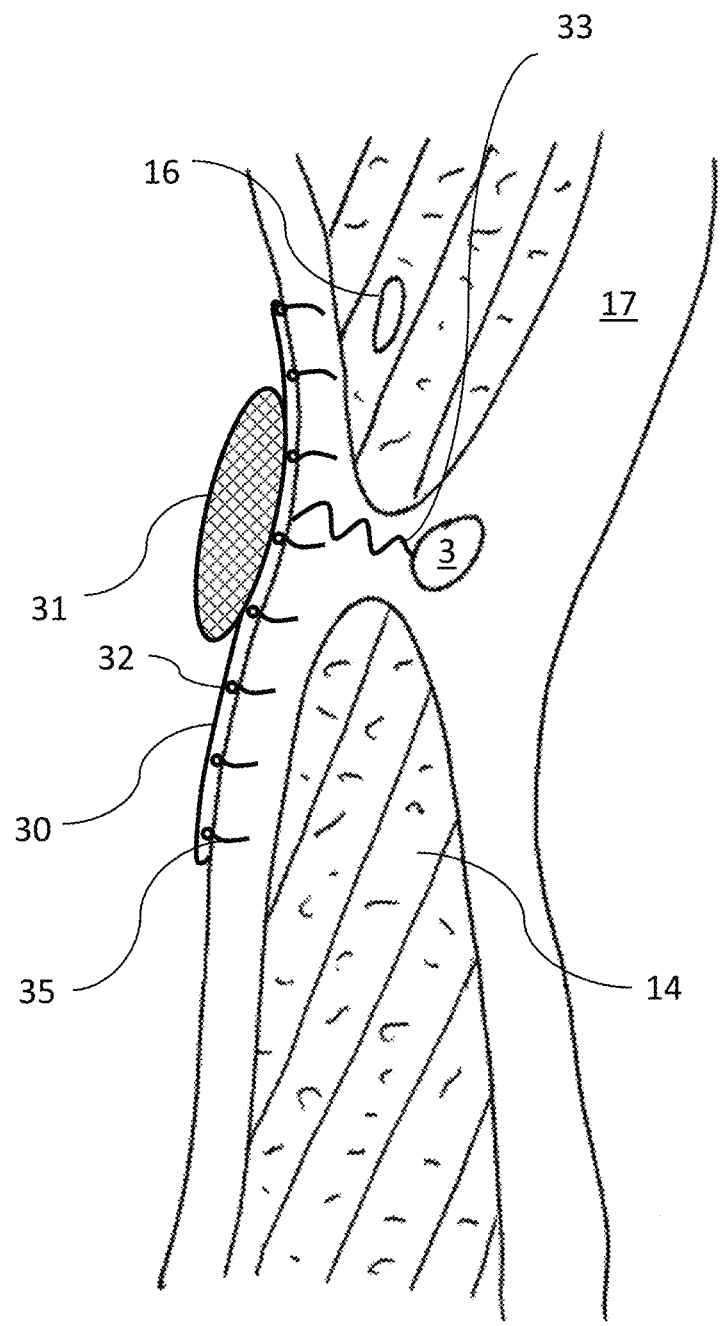
FIG. 8 shows a cross-sectional side view of yet another variation of the multi-electrode leadless pacemaker of the present invention as in FIG. 6.
Figure 10:
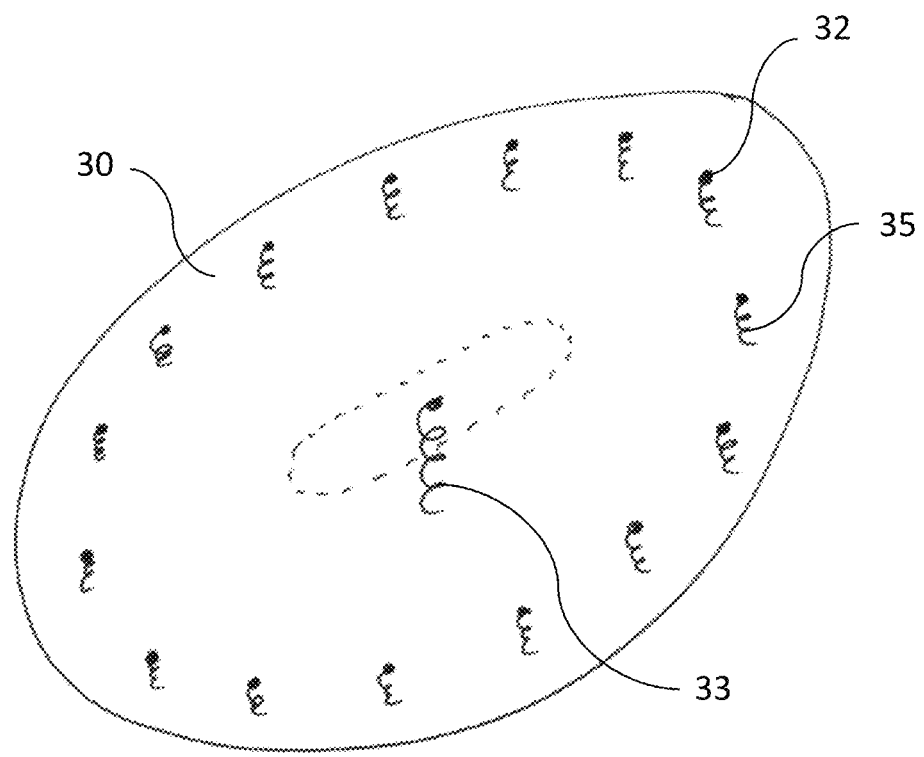
FIG. 10 is the bottom perspective view of the same as in FIG. 9.

FIGS. 8 and 10 show a sagittal view and a top view of a further advantageous variation of the embodiment shown in FIGS. 6 and 7. In this case, at least some or all of the individual electrodes 32 may be equipped with extension wires 35, extending away from the flexible member 30 towards the underlying cardiac tissue and configured to penetrate therein. Fixation screws or staples may also be used instead of some or all extension wires as seen in FIG. 10. The intent of such extension wires 35 is two-fold: (i) to improve long-term fixation of the device in place and (ii) to provide an improved electrical coupling between the leadless pacemaker of the invention and heart tissue at locations closer to the triangle of Koch and His bundle conduction pathways. In embodiments, all extensions 35 may be made of the same length, while in other embodiments, the length of individual extensions may be made different and optionally trimmable—depending on the expected location of the target conduction pathways. In embodiments, individual extension wires and/or fixation screws may be configured to penetrate the cardiac tissue to sufficient individualized depth to provide electrical connections to the controller suitable for delivering electrical stimuli to the cardiac tissue in a therapeutic mode of operation of the controller.

In further embodiments, the flexible member 30 may be made both flexible as well as malleable to an extent (as defined for example by the malleable leads of individual electrodes 32 embedded therein). The malleability of the flexible member or another method to provide the flexible member 30 in a predetermined or at least preferred shape may be advantageous in assuring that all electrodes 32 are placed in good and intimate contact with the underlying cardiac tissue.

At the same time, providing the flexible member in a predefined shape may be done without jeopardizing the ability of the flexible member to wrap in a tight fashion in order to be deployed through a delivery catheter. This may be achieved for example by using flexible shape memory materials such as Nitinol wires to be encapsulated in the flexible member 30 (not shown in the drawings) and configured to define its predetermined shape. Such Nitinol wires may be provided inside the body of the flexible member 30 as a standalone plurality of wires, as a wire framework. In further embodiments, Nitinol wires may also be used as electrical conductors to the individual electrodes 32, while in alternative embodiments at least some or all of the individual electrodes may be comprising dedicated electrical conductors selected to be made in a way to only conduct electrical signals and not impact the shape of the flexible member 30.

Embodiments of the invention described starting in FIG. 6 may be delivered and deployed in place either as a single self-contained unit as mentioned before or can be modified to facilitate deployment in stages. To that end, one, some or all individual electrodes 32 may be terminated with a small electrically conductive ring or a loop 36 configured to be slidingly engaged with a corresponding individual lead 37, which in turn may be equipped with a fixation screw 38 on a distal end thereof. The lead 37 may be made to have an outer electrical insulation along most of its length other than that close to its distal end.

Figure 11:
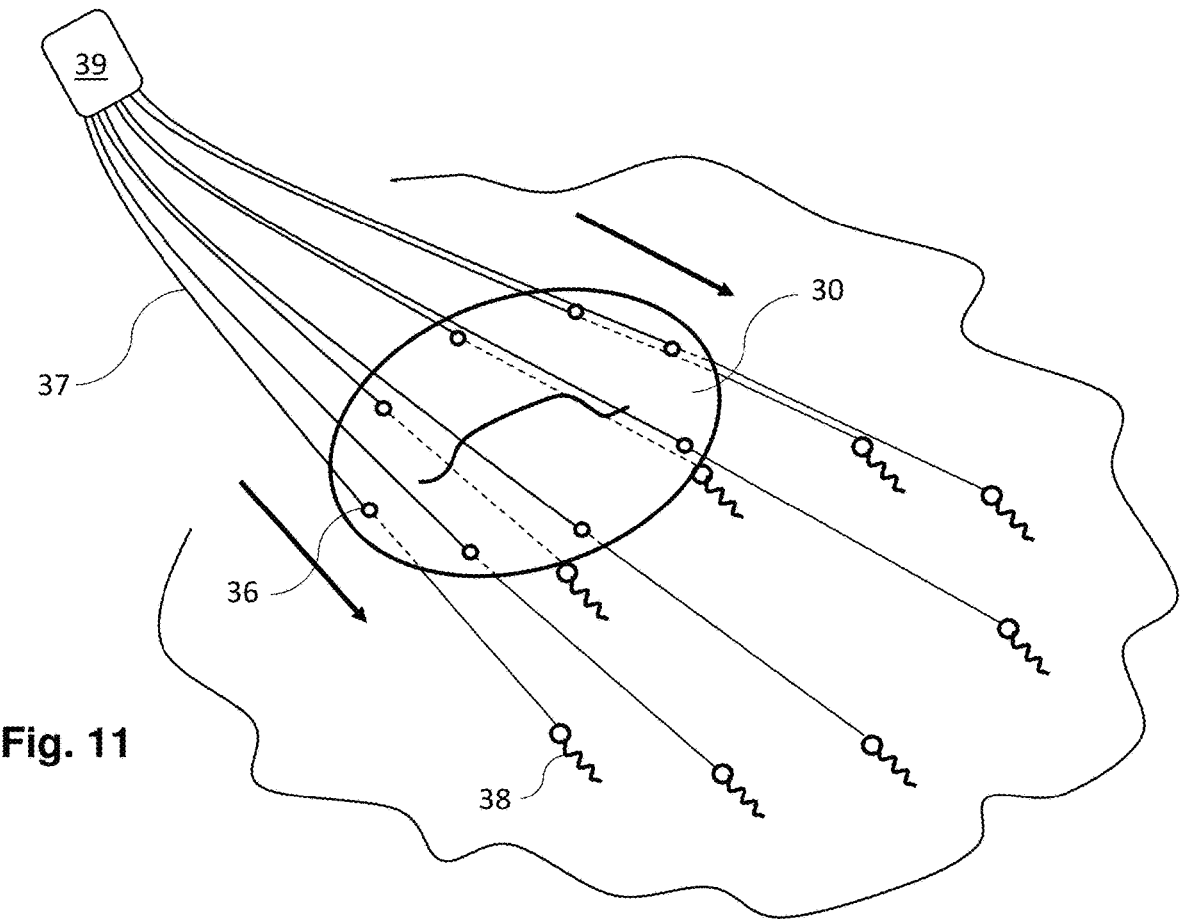
FIG. 11 is illustrating an intermediate stage of delivery of the leadless pacemaker shown in FIGS. 9 and 10.

To implant the leadless pacemaker of the invention, a plurality of individual leads 37 may be first implanted individually through a deployment catheter 39 (or in case of an open-heart surgery, directly engaged with the cardiac tissue one by one) so as to position individual fixation screws 38 at the expected locations of the target area of the cardiac tissue. Once positioned, the other remaining component of the system, namely the flexible member 30 incorporating the main pacemaker housing 31 and individual electrodes 32 may be advanced over the remaining section of the individual leads 37—see FIG. 11.

Figure 12:
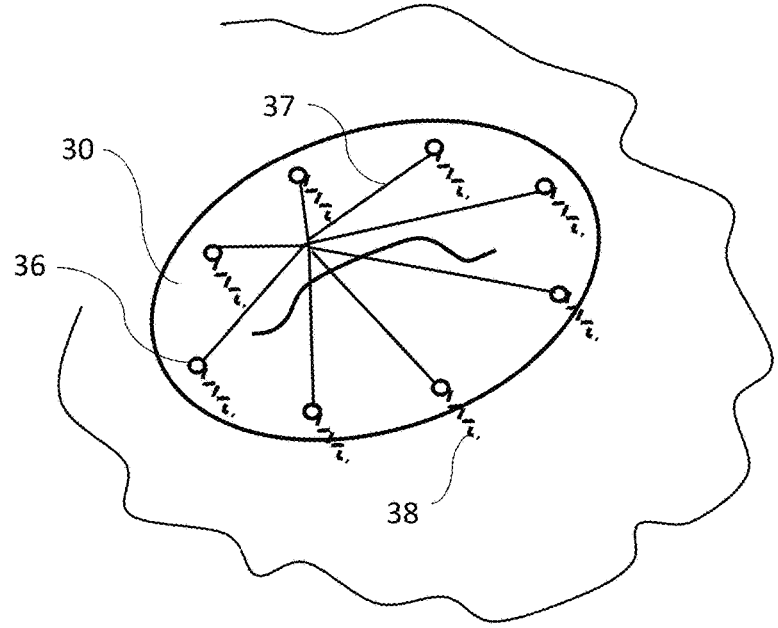
FIG. 12 shows a final stage of delivery of the same as in FIG. 11.

FIG. 12 shows a final step in the deployment of the leadless pacemaker of the invention, in which individual electrodes 37 are engaged both mechanically and electrically with corresponding individual electrodes 32 while providing a reliable fixation and electrical coupling with the target area of the cardiac tissue. Once the flexible member 30 is positioned in place, the remaining portion of the individual leads 37 may be trimmed and tied together to assure that the flexible member 30 remains in place.

Figure 13:
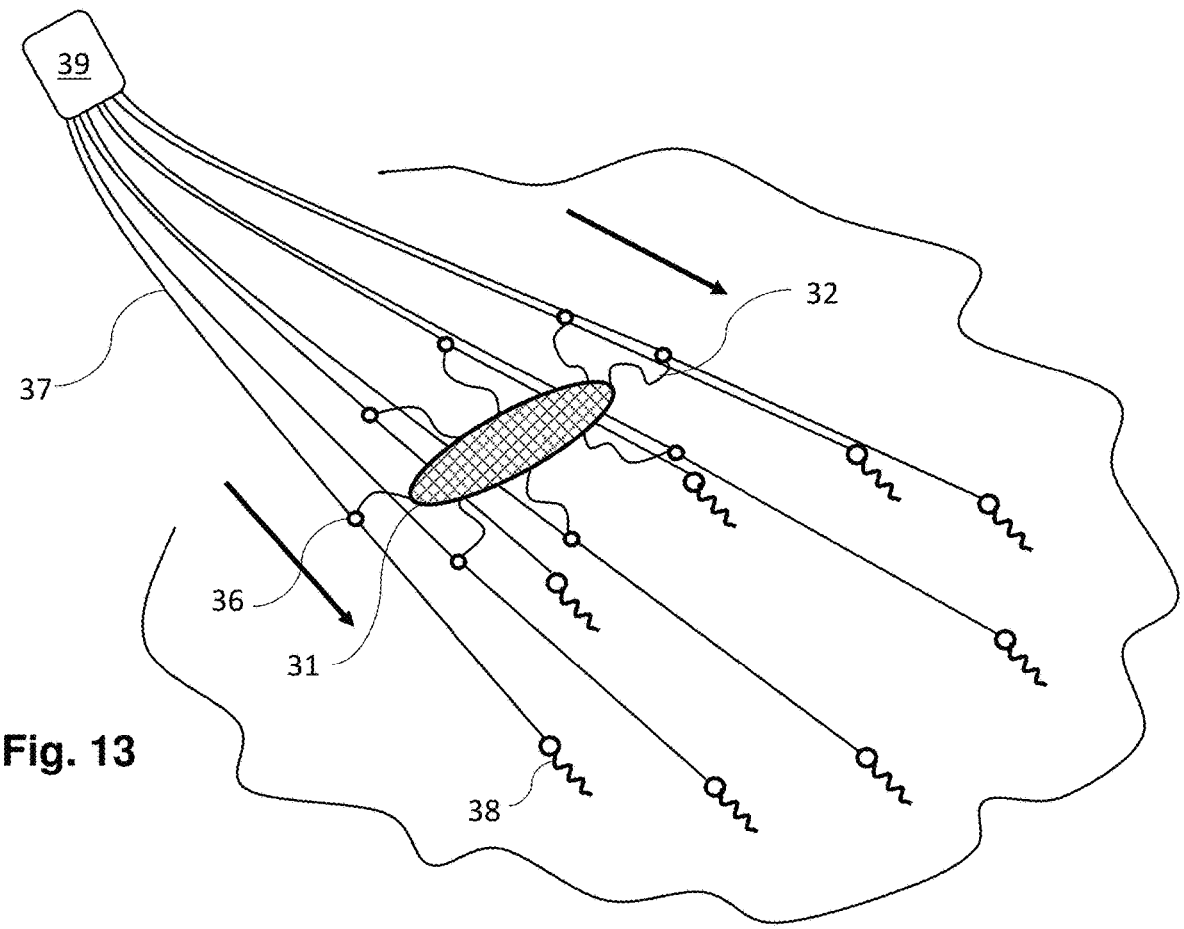
FIG. 13 is yet a further configuration of the leadless pacemaker of the present invention shown in an intermediate stage of deployment.
Figure 14:
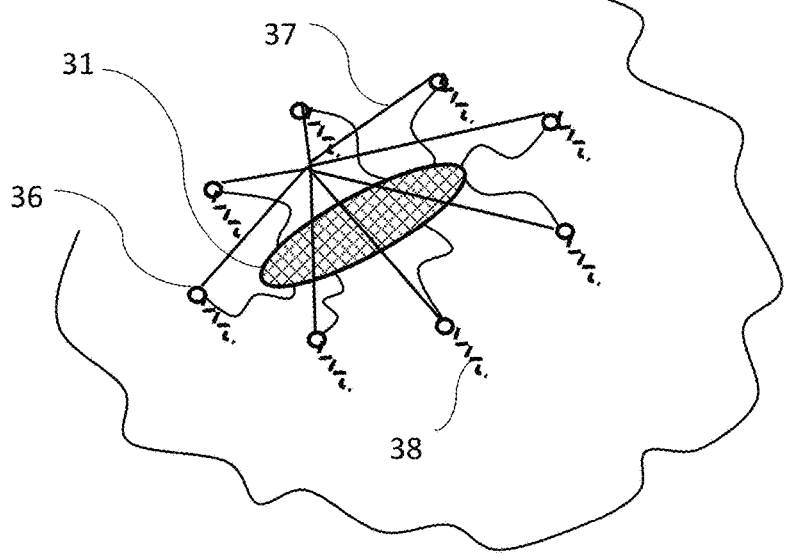
FIG. 14 shows a final stage of deployment of the leadless pacemaker of FIG. 13.

A further variation of these embodiments and the steps of its deployment are shown in FIGS. 13 and 14. In this case, the main rigid housing 31 is equipped with flexible electrodes 32, each terminating in an electrically conductive ring 36. There is no flexible member 30 in this configuration, although individual leads 37 are present.

In the first several steps of the implantation procedure (FIG. 13), individual leads 37 may be deployed one at a time using conventional methods—such as through the delivery sheath 39. Distal ends of the individual leads 37 may again be equipped with fixation screws 38 so as to position thereof with sufficient attachment to the cardiac tissue at the target area. Once individual leads are deployed, the main housing 31 and individual electrodes 32 may be moved into position by rings 36 sliding along the corresponding individual leads 37—see FIG. 14. Once the main housing 31 is in position, the leads 37 may be trimmed or otherwise truncated and optionally collected together in a single spot over the main housing 31—so as to assure its secure placement in the heart.

The main advantage of this approach is the lack of flexible member 30 making it less bulky in size and facilitating a less invasive implantation. Another advantage is that the location of each individual fixation screw 38 does not have to match precisely to the corresponding location on the flexible member 30—so that the implantation procedure requires less precision to accomplish.

Left Bundle Branch Configurations of the Leadless Pacemaker

As seen previously in FIG. 3, His bundle 3 bifurcates into a left 4 and right 4' bundle branch as it leaves the area of the right atrium and penetrates the atrio-ventricular septum. It may be desirable for certain subjects to implant the leadless pacemaker of the invention 40 in a way to access only the left bundle branch 4, only the right bundle branch 4' or both left and right bundle branches 4 and 4', but not the His bundle directly. This need may arise for example in situations of a left bundle branch block, which may be accompanied by a low ejection fraction and/or ventricular dyssynchrony, possibly leading to low cardiac output.

Figure 15:
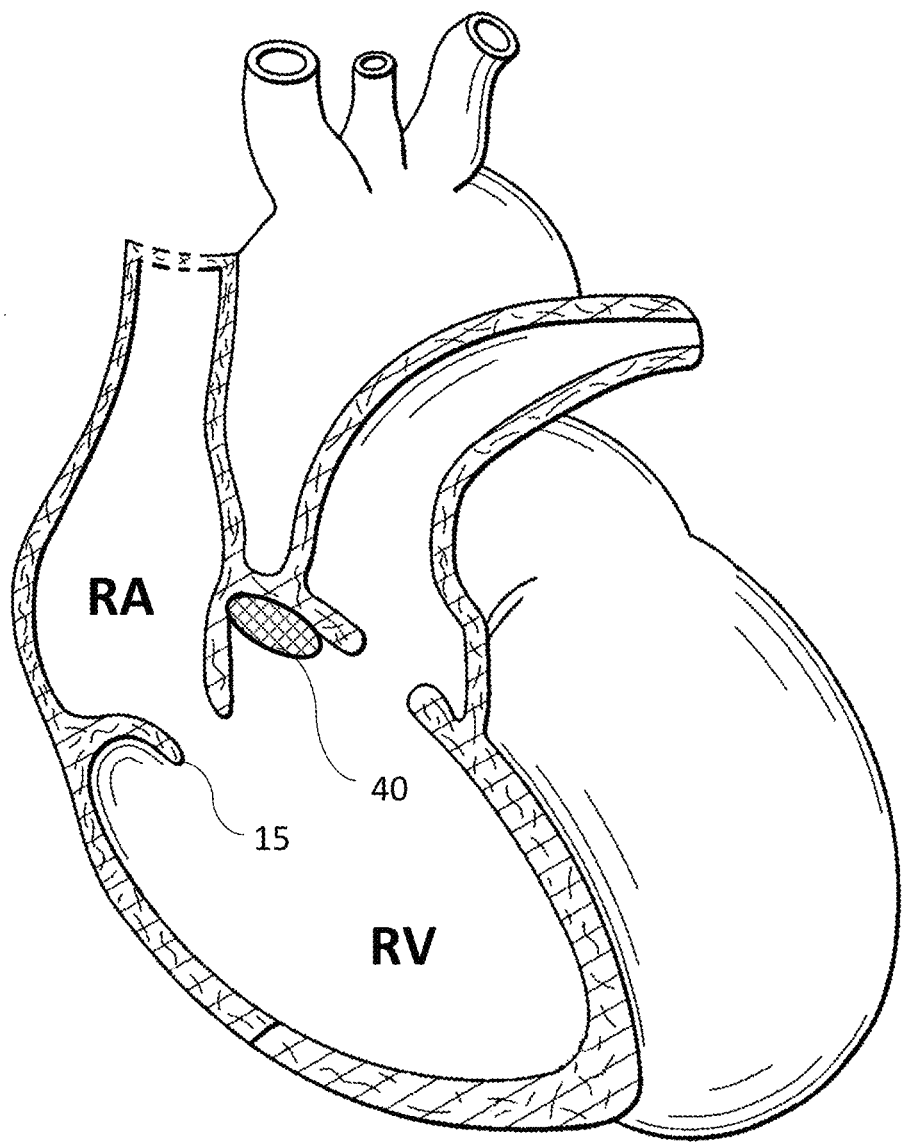
FIG. 15 shows a cross-sectional general view of the heart illustrating an alternative position of the leadless pacemaker of the present invention capable of reaching His bundle as well as left bundle branch and right bundle branches from a right ventricle.
Figure 16:
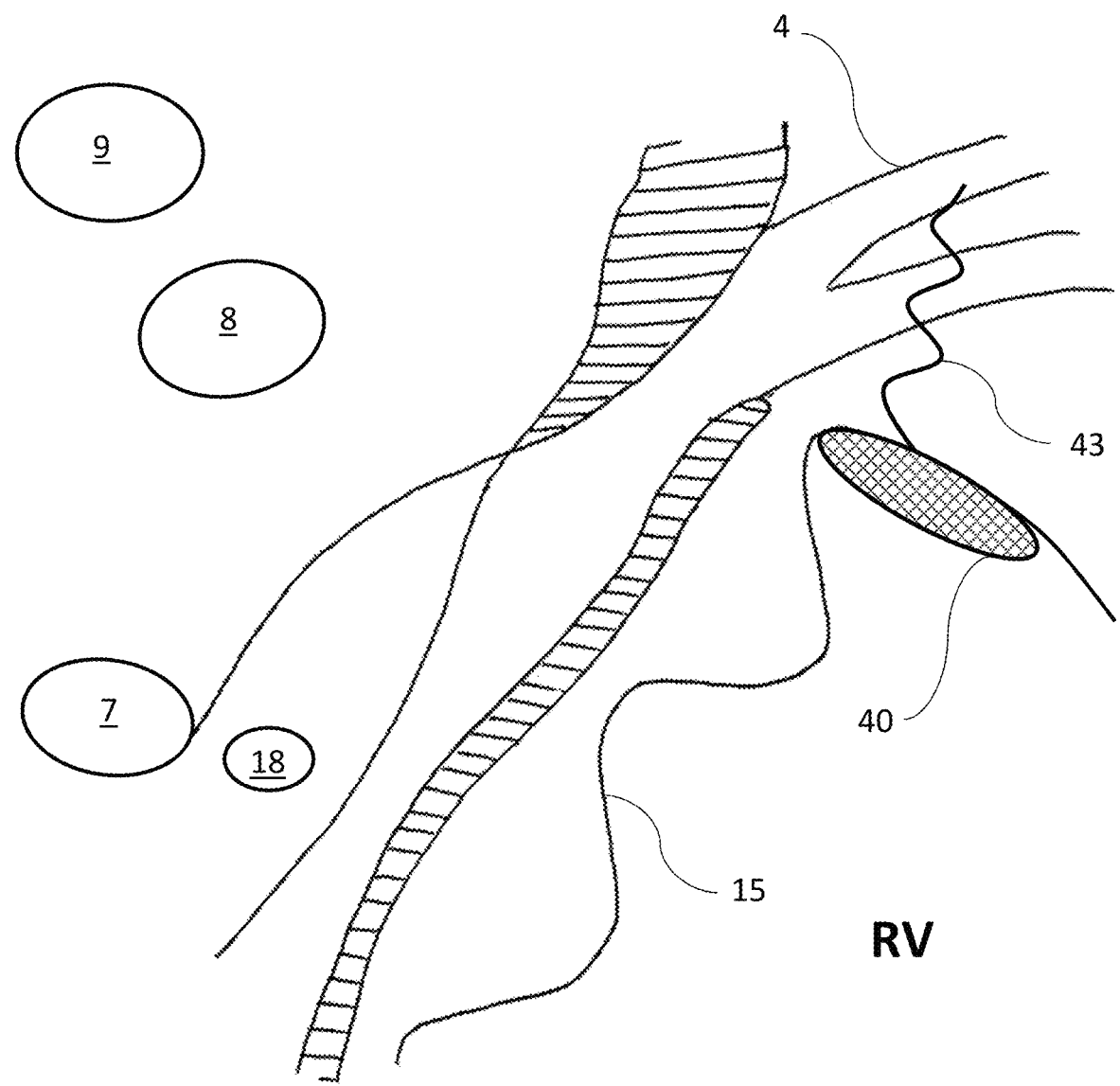
FIG. 16 is a schematic view of a close-up showing the leadless cardiac pacemaker reaching a left bundle branch.

In order to reach the bundle branches in that case, the leadless pacemaker of the invention 40 may be implanted in an alternative location, namely at the top of the right ventricle under one of the leaflets of the tricuspid valve 15—see FIG. 15. Care needs to be taken so as to not have the pacemaker 40 interfere with the leaflets of the tricuspid valve, as can be appreciated by those knowledgeable in the art. As shown in a close-up in FIG. 16, the pacemaker 40 may be equipped with a fixation screw 43, which may be long enough and configured to reach the left bundle branch 4. Other individual electrodes are not shown in this view but may be configured to reach other areas of the conductive pathways of the triangle of Koch and His bundle and may be used for sensing and pacing operations.

Figure 17:
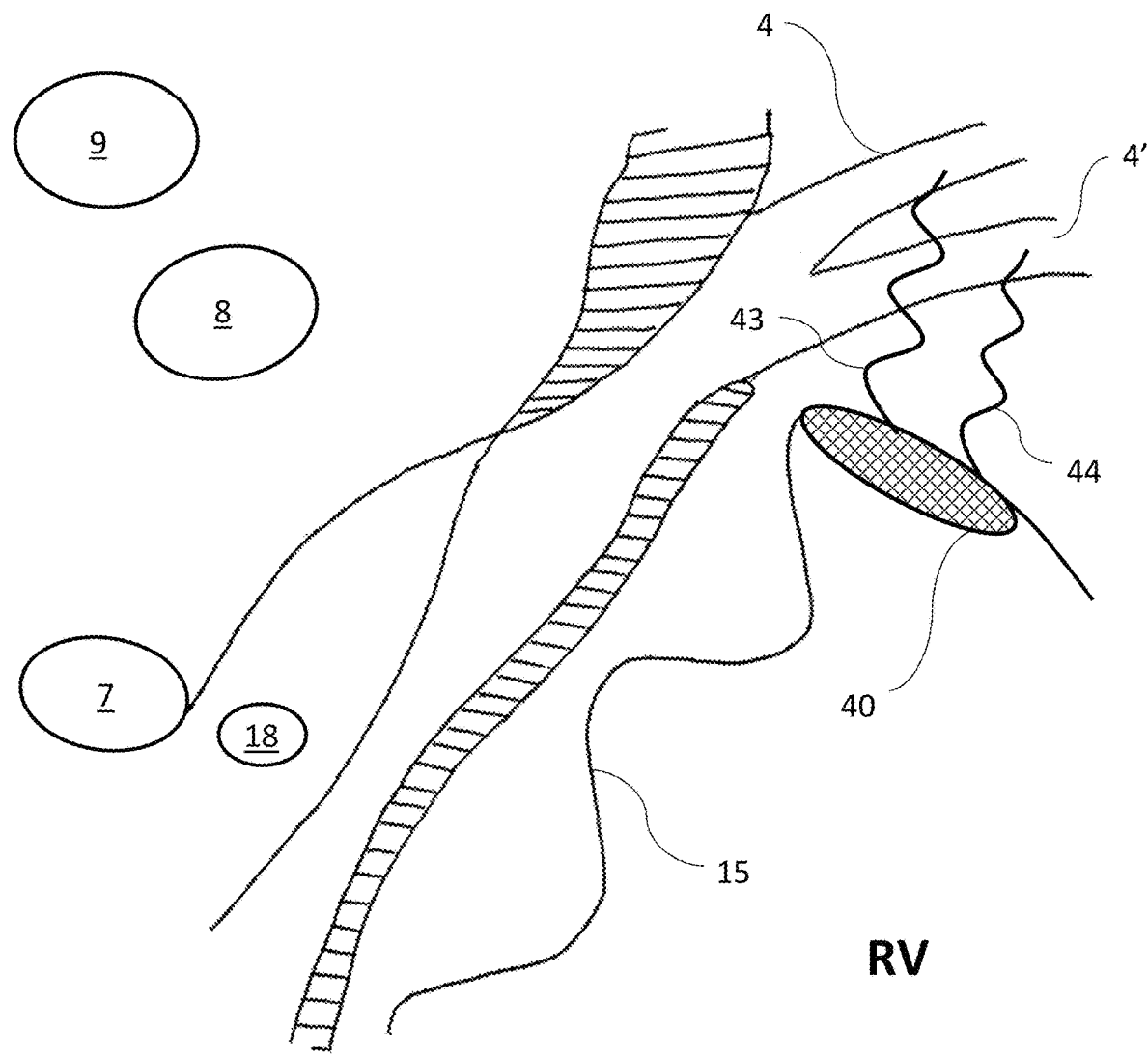
FIG. 17 is the same as in FIG. 16 wherein the leadless cardiac pacemaker is configured for reaching either left bundle branch, right bundle branch, or both left and right bundle branches.

A further embodiment of the invention is seen in FIG. 17. In this case, two fixation screws 43 and 44 may be provided in order to reach the corresponding left 4 and the right 4' bundle branches if needed for clinical reasons. In alternate embodiments, a single fixation screw 43 in a left bundle branch 4 may be supplemented with one or more individual electrodes configured to reach the right bundle branch 4' (not shown in the drawings).

Implantation Approaches for the Leadless Pacemaker of the Invention

Figure 18:
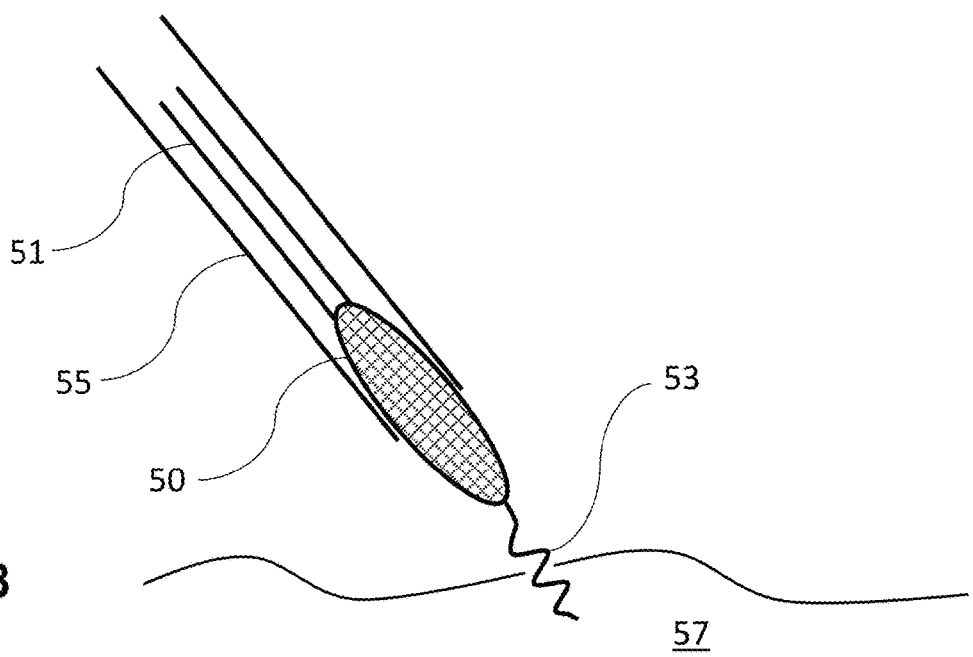
FIG. 18 shows an initial stage of minimally invasive delivery of the leadless pacemaker of the invention into the heart.
Figure 19:
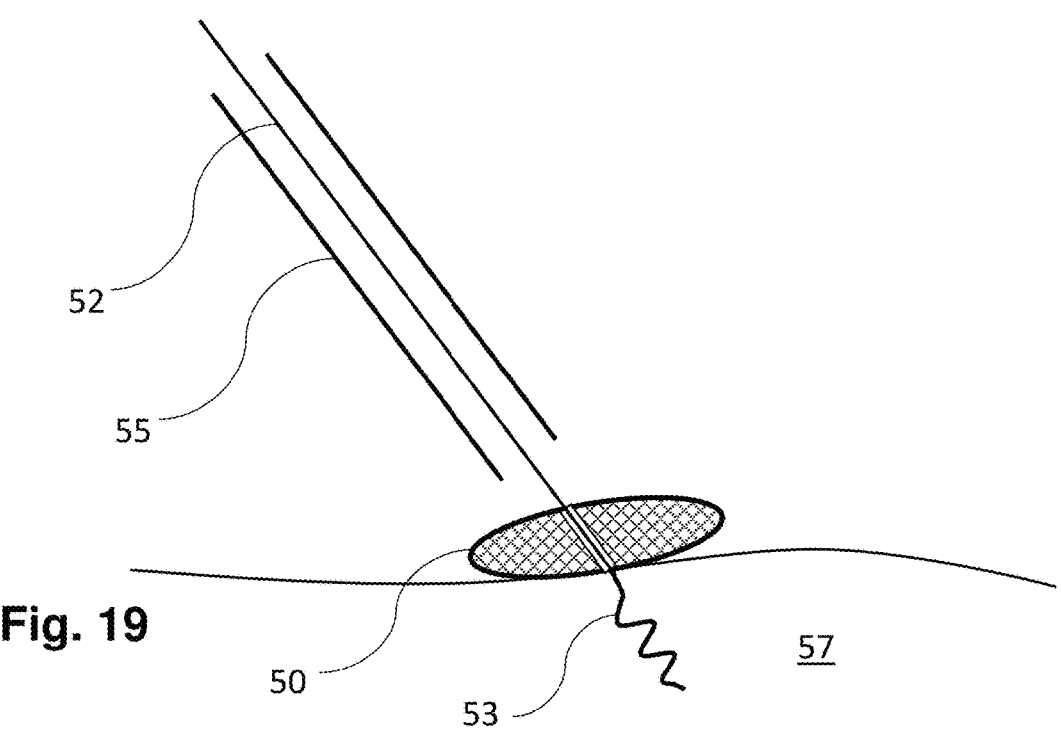
FIG. 19 shows a more advanced stage of the same delivery process.
Figure 20:
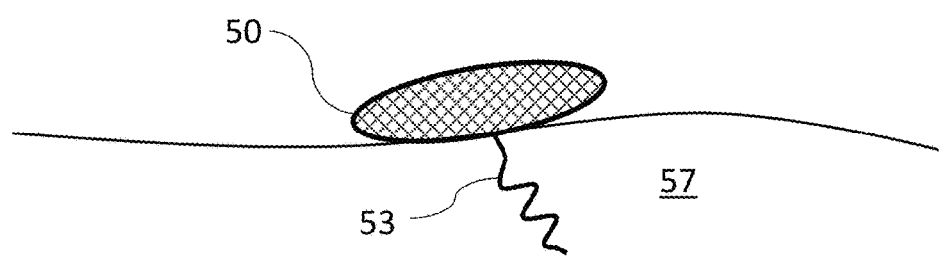
FIG. 20 shows a final configuration following the delivery of the leadless cardiac pacemaker and attachment thereof to the cardiac tissue.

FIGS. 18 through 20 depict further details of the minimally invasive implantation approach for the leadless pacemaker 50 of the present invention. As described above, a delivery catheter 55 may be first inserted via a percutaneous or local tissue cutdown procedure into a major blood vessel and advanced to the area of the right atrium of the heart via an inferior or a superior vena cava. The distal end of the delivery catheter 55 may then be positioned in the vicinity of the target area of the heart 57 located at the triangle of Koch or His bundle and surrounding areas. A fixation screw 53 may be first advanced to reach the target area 57. As the main housing of the leadless pacemaker 50 may be made to have an elongated shape in order to fit into a small diameter delivery catheter 55, initially the long axis of the pacemaker 50 may be aligned with the long axis of the fixation screw—see FIG. 18. This may be achieved in a variety of ways, such as:

a. the fixation screw 53 and its activation wire 52 may be placed in parallel and not interfere with the leadless pacemaker 50 while in the delivery catheter 55 and its corresponding pusher tube 51;

b. the fixation screw 53 may reside inside an opening in the leadless pacemaker 50 which in turn may reside inside the delivery catheter 55, in which case the pusher tube 51 may contain a lumen housing the activation wire 52 of the fixation screw 53;

c. the housing of the leadless pacemaker 50 may contain a passage sized to allow only the activation wire 52 to reside therein but not a larger diameter fixation screw 53, in which case the fixation screw 53 may be located distally in front of the leadless pacemaker 50 while inside the delivery catheter 55, or any other suitable configurations as may be understood by those skilled in the art, as the present invention is not limited in this regard.

Depending on the specific configuration of the delivery system and the interaction of the fixation screw 53 with the leadless pacemaker 50, after positioning of the distal end of the delivery catheter 55 adjacent to the target area 57, the fixation screw 53 may be first advanced towards the cardiac tissue 57 and turned to engage therewith using the activation wire 52.

Once the connection between the fixation screw 53 and the cardiac tissue is established, the leadless pacemaker 50 may be advanced distally to be positioned next to the fixation screw 53—see FIG. 19. This may involve in some cases a quarter-turn rotation of the leadless pacemaker 50 to position its middle portion next to the fixation screw 53. Either one or both the leadless pacemaker 50 and/or the fixation screw 53 may have engagement elements to establish a secure connection therebetween once both are in their respective final positions—see FIG. 20. After achieving a proper position of both components 50 and 53, the activation wire 52, the pusher tube 51, and the delivery catheter 55 may be withdrawn.

Figure 21:
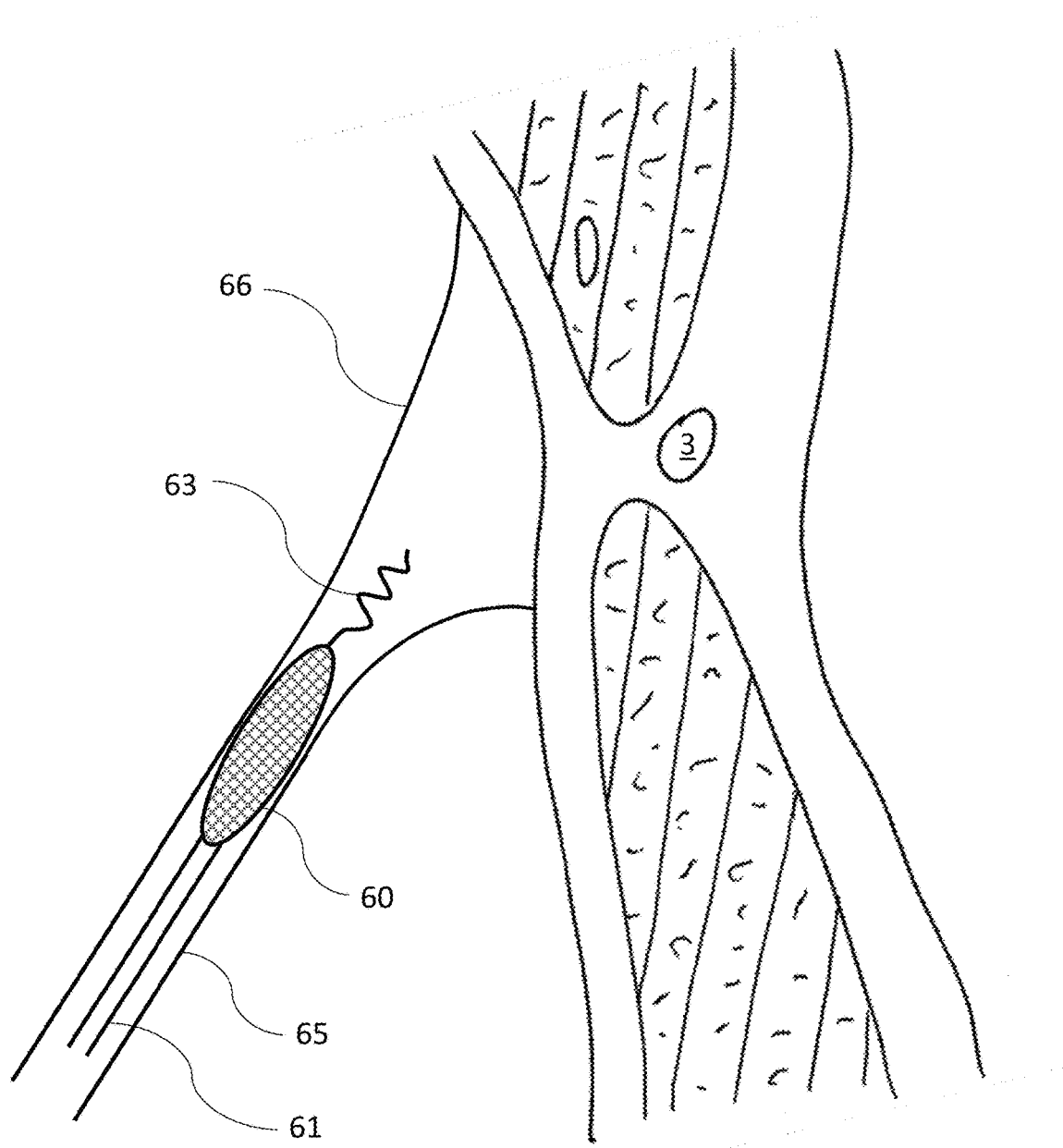
FIG. 21 shows a cross-sectional view of an alternative delivery procedure for deployment of the leadless pacemaker of the present invention using a suction cup.
Figure 22:
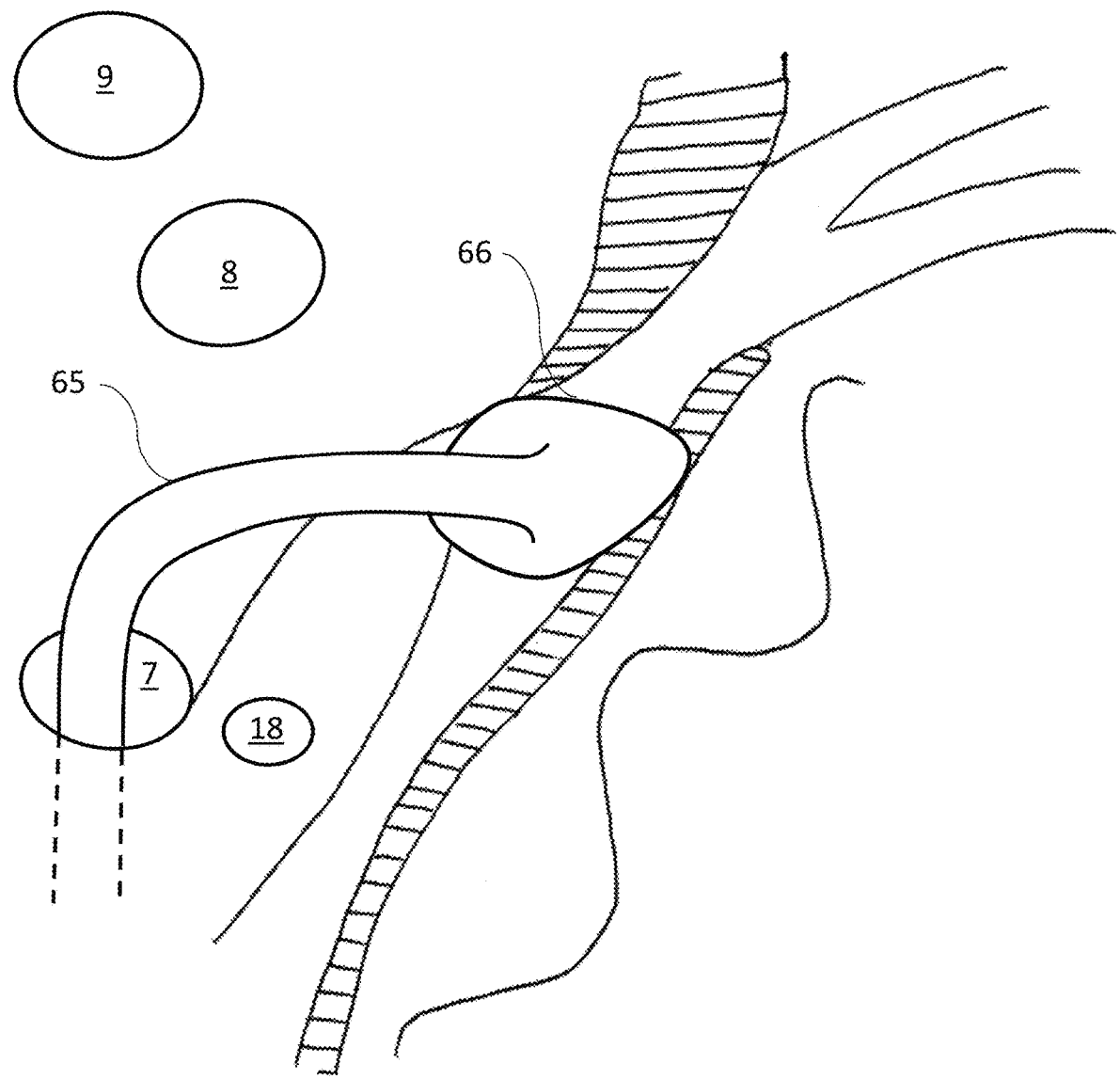
FIG. 22 shows a top view of the same as in FIG. 21.

FIGS. 21 and 22 show another yet embodiment of the delivery approach, in which the delivery catheter 65 is equipped with a distal suction cup 66 configured to allow a temporary engagement of the distal end of the delivery catheter 65 with the target area tissue. In embodiments, the suction cup 66 may be made to be sufficiently flexible to allow it to be collapsed and fitted (folded or otherwise compressed) into the percutaneous access sheath at the entry point of the delivery catheter 65 into the vasculature of the subject. The edge of the suction cup 66 may be made supple enough to assure vacuum-tight engagement with the cardiac tissue, while at the same time optionally containing an expansion member to assure its opening when allowed by surrounding space. One example of a suitable expansion member may be a ring made of a shape memory wire or a shape memory polymer material (not shown in the drawings). Once the distal end of the delivery catheter 65 has passed through a smaller blood vessel and entered the vicinity of the right atrium, for example via an inferior vena cava as seen in FIG. 22, the suction cup 66 may be allowed to expand so as to position thereof over the target area for implantation of the leadless pacemaker 60.

Suction may then be applied to the interior space of the delivery catheter 65, while allowing the leadless pacemaker 60 and the fixation screw 63 to be advanced forward via the pusher tube 61 or by other suitable means. Application of suction to the interior space of the delivery catheter 65 and the interior space of the suction cup 66 allow advantageously to first removably engage the delivery system with the heart tissue so as to confirm the location thereof—prior to the permanent deployment of the leadless pacemaker 60. In case the location of the delivery catheter 65 is determined to be inaccurate, the suction can be discontinued and the suction cup 66 may be repositioned until a proper location for further implantation of the device is confirmed.

A further advantage of the use of the suction cup 66 is in pulling in and retaining the target area cardiac tissue in close vicinity and in front of the fixation screw 63, which facilitates its reliable engagement with therewith. As can be appreciated by those skilled in the art, the walls of the delivery catheter 65 need to be made with a sufficient hoop strength to resist collapse upon applying a suitable level of vacuum to the interior thereof. This may be accomplished by either one or a combination of (i) incorporating a wire reinforced braided structure within the wall of the delivery catheter 65, (ii) providing ribs or other interior features to avoid collapse of the interior space, (iii) using internal members to prevent such collapse, for example, the pusher tube 61, or by other suitable design choices.

Figure 23:
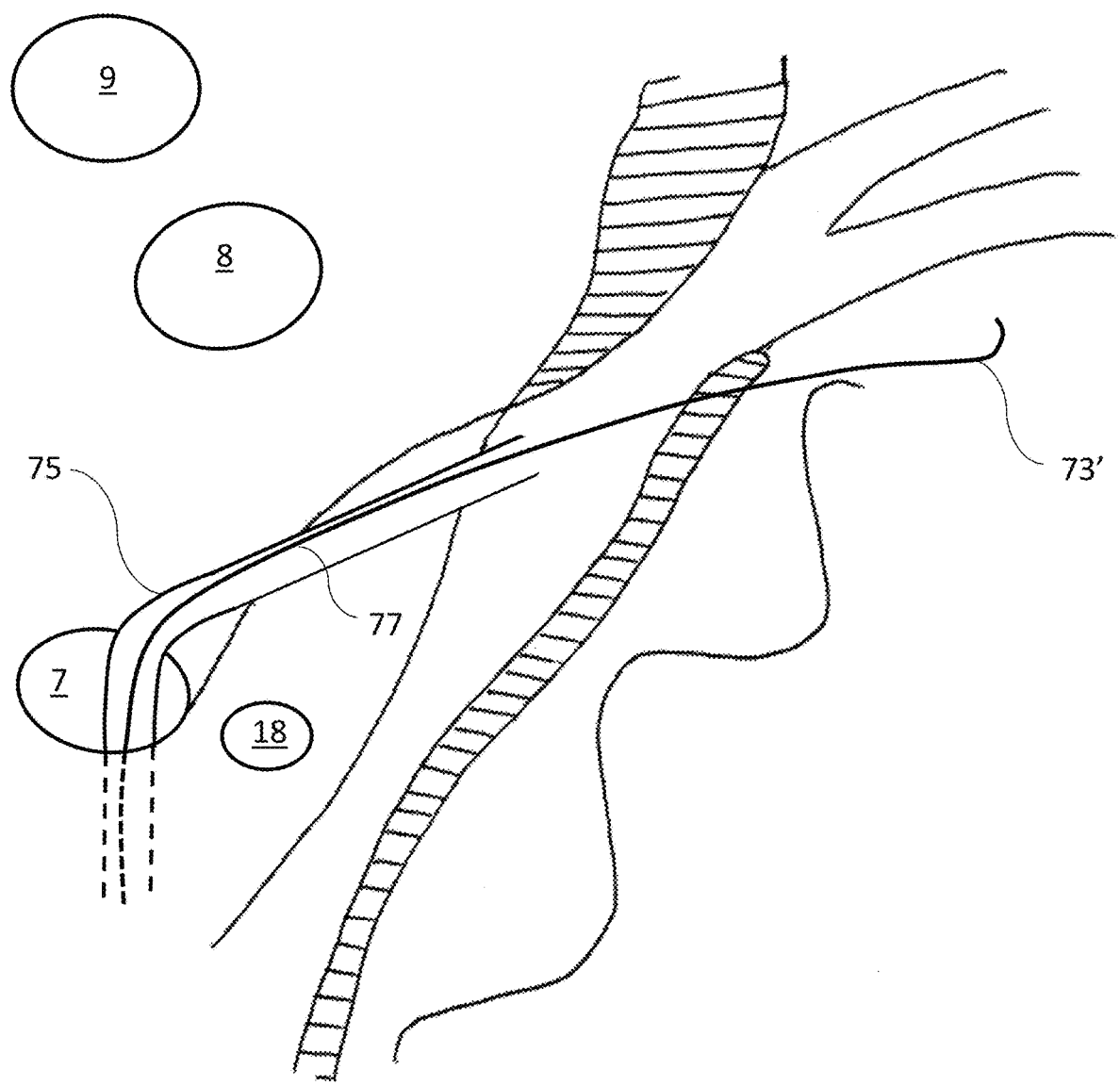
FIG. 23 shows yet another alternative procedure of delivery of the leadless pacemaker or components thereof into position and attachment to the target heart tissue.
Figure 24:
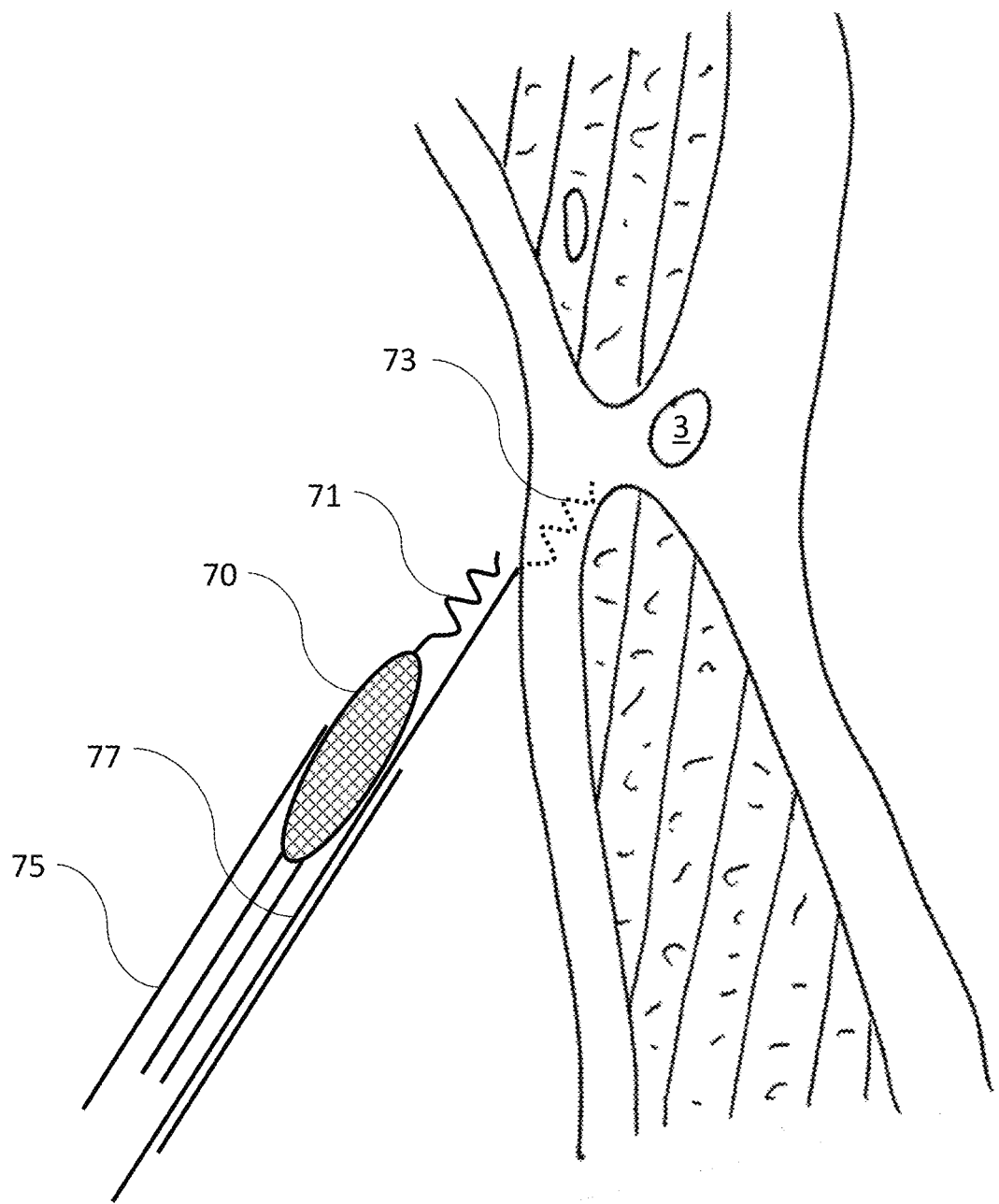
FIG. 24 shows a cross-sectional side view of yet a further alternative procedure of delivery of the leadless cardiac pacemaker of the present invention, FIG. 25 schematically shows a top view of the same as in FIG. 24.
Figure 25:
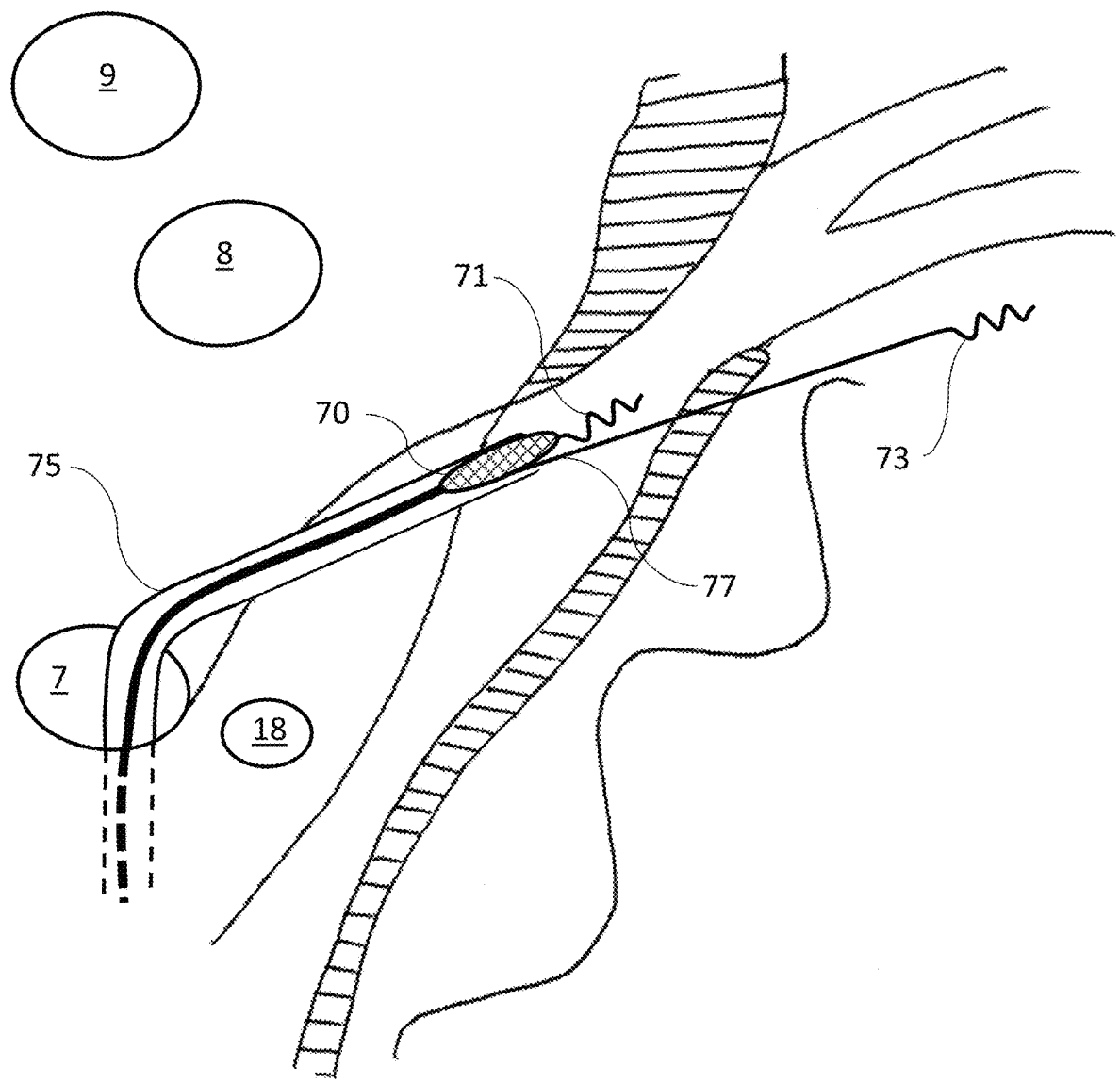

Another yet delivery approach is shown schematically in FIGS. 23-25. In order to achieve the same temporary engagement of the delivery system with the target area in the heart and to verify the placement location before a permanent placement of the leadless pacemaker 70, a preliminary step of positioning a first fixation screw 73 or a stiff straight or curved distal end 73' may be taken. In embodiments, this reversible placement of a first fixation screw 73 or distal end 73' may be made in one of the following two approaches:

a. the first removable fixation screw 73 or distal end 73' may be used as a temporary guide towards the target area and may be removed after implantation of the leadless pacemaker 70 is complete, in which case it may be positioned in ventricular tissues or elsewhere in the vicinity but yet outside the target area (not at the His bundle for example) so as not to interfere with the subsequent placement of the second and permanent fixation screw 71 for securing the leadless pacemaker 70 in place (see FIGS. 23 and 24). A reversibly placed first fixation screw 73 may be delivered via a dedicated first delivery catheter of a smaller diameter—once in place, the first delivery catheter may be removed and the second delivery catheter 75 containing the leadless pacemaker 70 may be inserted using a guiding wire 77 to reach the vicinity of the first fixation screw 73; or b. the first fixation screw is intended to remain in place and become a part of the leadless pacemaker 70 individual electrodes group, in which case it may be placed to reach His bundle or other desirable locations in the target area (see FIG. 25).

Tissue Engagement Elements of the Leadless Pacemaker of the Present Invention

In addition to external tissue engagement components such as fixation screws and staples as described above, the present invention also contemplates incorporation of tissue fixation elements inside of the housing of the leadless pacemaker itself. This general approach may be advantageous since the tissue engagement elements may be configured for operation in two positions: (i) a collapsed position, in which none of the tissue engagement elements are protruding beyond the bounds of the housing of the leadless pacemaker; and (ii) as expanded position in which tissue engagement elements are caused to emerge from the housing of the leadless pacemaker and engage with the adjacent cardiac tissue upon moving the first housing portion closer to the second housing portion. In this case, the tissue engagement elements may be first placed in a collapsed position so that the leadless pacemaker may be advanced through the vasculature in a small diameter delivery catheter. Once in the vicinity of the target area, the tissue engagement elements may be activated to secure the device in place and provide electrical coupling to the target area of the heart.

In embodiments, conventional shape memory hooks and claws may be incorporated with the housing of the leadless pacemaker as was described above. The release of the device from the tightly surrounding tube of the delivery catheter may be used to free up these elements and allow them to expand and engage with the cardiac tissue.

Figure 26:
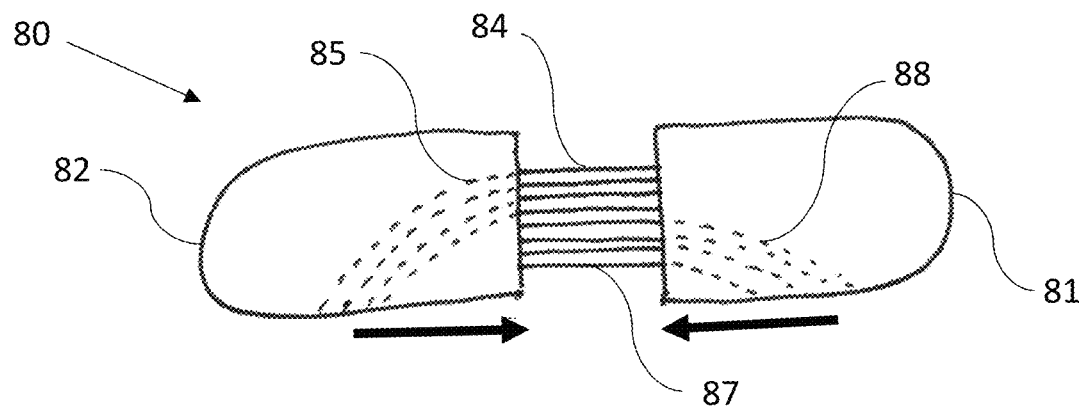
FIG. 26 is a side view of yet another configuration of the leadless cardiac pacemaker of the present invention in its expanded state.
Figure 27:
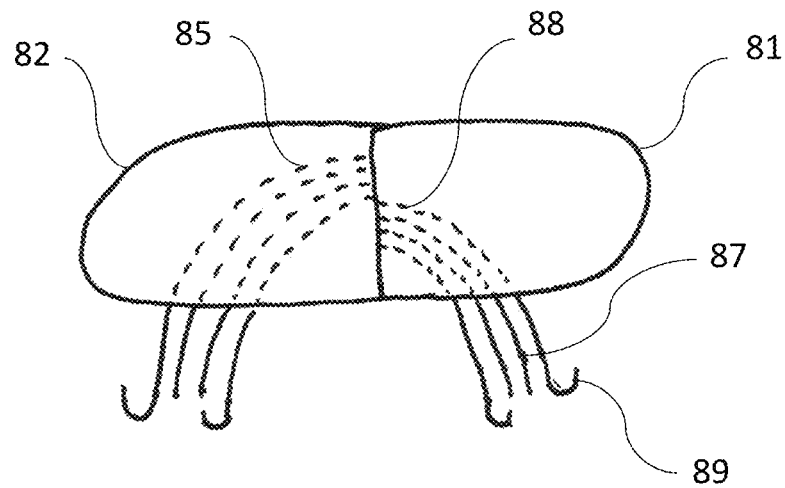
FIG. 27 is a side view of the same wherein the cardiac pacemaker is in its compressed state.
Figure 28:
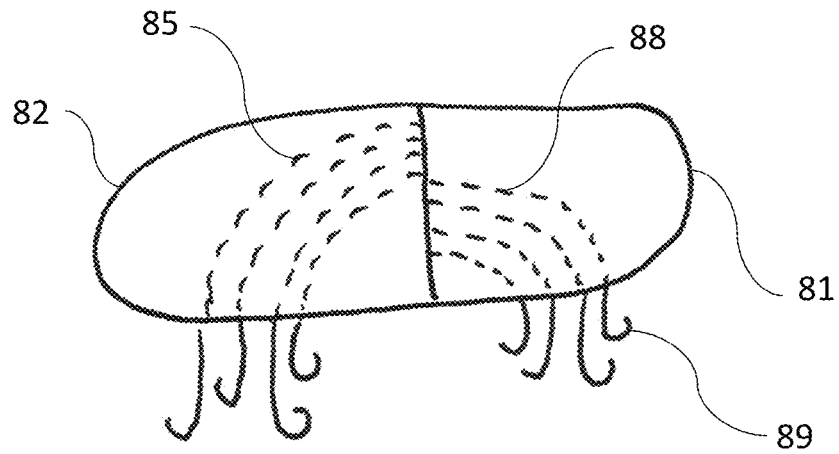
FIG. 28 shows the same as in FIG. 27 but with all emerging leads forming engagement hooks when deployed.

Further embodiments of the tissue engagement elements are illustrated in FIGS. 26-28, where the housing of the leadless pacemaker 80 may be split into a hermetically sealed first housing portion 81 and a hermetically sealed second housing portion 82. The first housing portion 81, in turn, includes a first plurality of individual electrodes 84 permanently affixed thereto and slidably residing in a second plurality of corresponding channels 85 of the second housing portion 82. In a similar fashion, the second housing portion 82 may include a second plurality of individual electrodes 87 permanently attached thereto and slidably residing in a first plurality of corresponding channels 88 of the first housing portion 81.

In further embodiments, only one of the first housing portion 81 or the second housing portion 82 may include a corresponding plurality of the individual electrodes 84 or 87 as the invention is not limited in this regard.

The leadless pacemaker 80 may have a first longitudinally expanded state (see FIG. 26) and a second compressed state (see FIG. 27 or 28). In the first state, the two housing portions 81 and 82 are extended away from each other so as to cause all of the individual electrodes 84 and 87 to reside within the bounds of the leadless pacemaker 80 and not extend beyond thereof.

The first and/or the second plurality of channels 85 and 88 may be made curved so as to direct the distal sections of individual electrodes 84 and 87 towards one side of the leadless pacemaker 80. The first housing portion 81 may also be connected to the second housing portion 82 by a flexible umbilical cable (not shown) in order to (i) provide electrical communication between both portions of the pacemaker 80 and (ii) limit the extent of travel of one housing portion relative to the other. In further embodiments, all electronic components of the leadless pacemaker 80 may be located in either the first housing portion 81 or the second housing portion 82 so there is no need for any electrical connections between thereof. In other embodiments, the length of each housing portion may be about equal to the other housing portion while in further embodiments, one of the housing portions may be made longer and contain a greater number of electronic components than the other as the invention is not limited in this regard.

Also contemplated within the scope of this invention is a removable spacer (not shown) positioned between the first and second housing portions, which may be used to prevent premature movement of the housing portions closer to each other.

Delivery of the pacemaker 80 is envisioned to start when both housing portions 81 and 82 in their extended position so as to contain all individual electrodes 84 and 87 within the internal space thereof, such as within channels 85 and 88. The diameter of the housing portions 81 and 82 may be made to be suitable for minimally invasive delivery via a delivery catheter as described above. The leadless pacemaker 80 is envisioned to then emerge from the distal end of the delivery catheter and located next to a target area within a heart optionally guided by any one or more of the known imaging techniques mentioned elsewhere in this description.

Once the pacemaker 80 is placed at the intended location, one or both housing portions 81 and 82 may be activated to move towards one another so as to bring the device to its collapsed position as indicated by arrows in FIG. 26. As both housing portions are advanced to be closer to each other, the individual electrodes 84 may emerge one at a time or altogether from their corresponding channels 85. As the position of the leadless pacemaker 80 may be selected to orient the openings of the second plurality of channels 85 to face the nearby cardiac tissue, emerging first plurality of electrodes may be directed by the second plurality of channels 85 to penetrate into the cardiac tissue at the target area of the heart. Similarly, the second plurality of individual electrodes 87 may be directed by their respective first plurality of channels 88 to emerge from within the first housing portion 81 and penetrate into the adjacent area of the cardiac tissue.

The geometry and length of the individual electrodes 84 and 87 and their respective channels 85 and 88 may be selected to position the ends of individual electrodes within the desired depth into the target area of the heart so as to facilitate cardiac sensing and stimulation operations as described above.

To further secure the leadless pacemaker 80 at the implantation site, one, some (FIG. 27) or all (FIG. 28) distal ends of the individual electrodes 84 may be configured to form hooks or claws at the same or different depths once released from the channels 85 and 88—in order to firmly engage with the underlying cardiac tissue.

Figure 29:
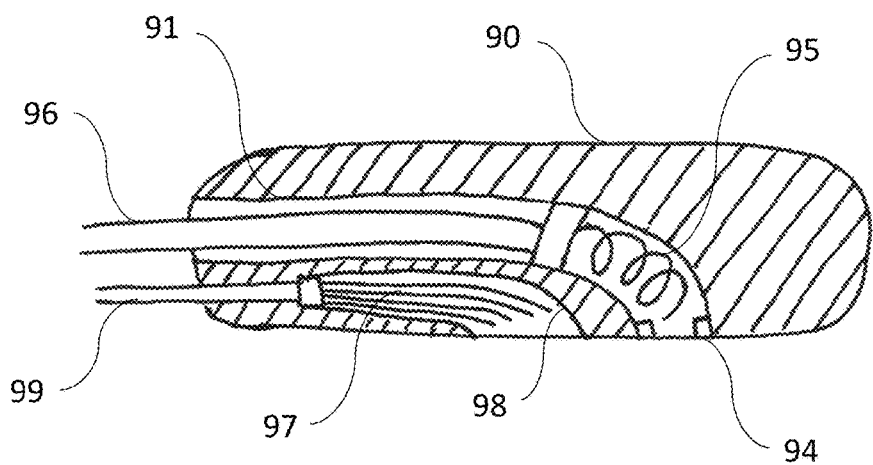
FIG. 29 shows yet another configuration of the leadless implantable pacemaker of the present invention with movable emerging attachment screw and multiple leads shown during initial stages of implantation.
Figure 30:
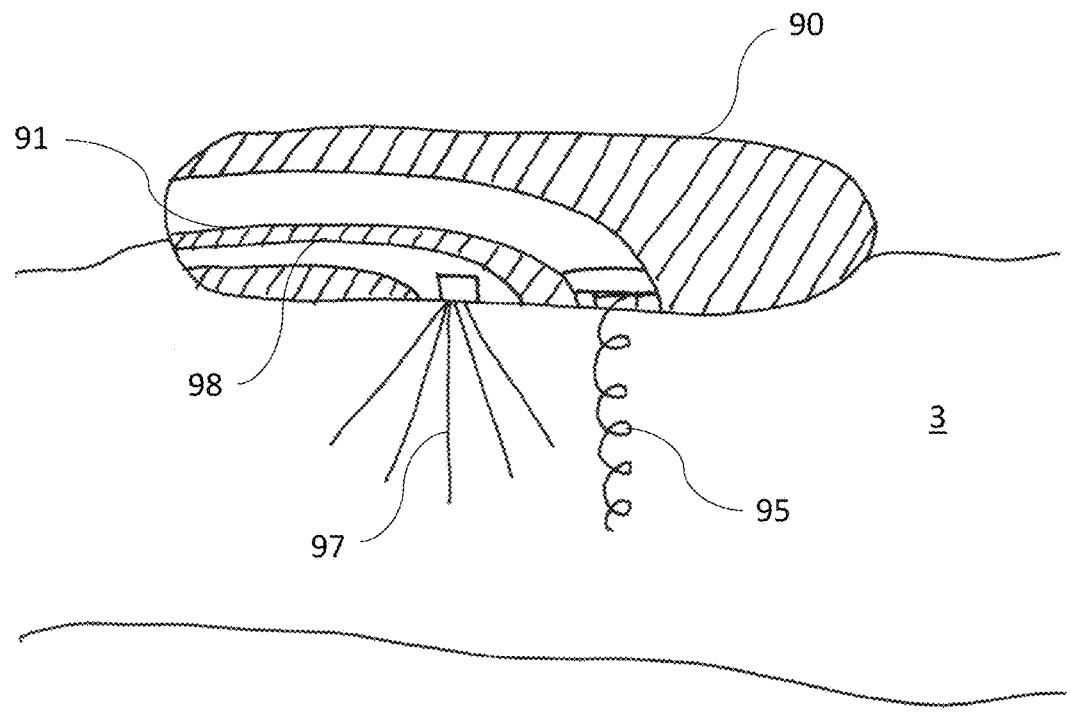
FIG. 30 shows the same as in FIG. 29 but in a final stage of deployment.

Another yet design configured for convenient implantation and reliable attachment to the adjacent cardiac tissue is shown in FIGS. 29 and 30. The leadless pacemaker 90, in this case, is made to contain a first inner channel 91 with a curved end 93 having an opening in a middle portion of the leadless pacemaker 90. An optional mechanical stop 94 may be provided near the opening of the curved end 93. A fixation screw 95 may be positioned within the first channel 91 such as to not extend beyond its bounds in the initial deployment position. The position and rotation of the fixation screw may be controlled via a releasably attached first pusher 96, configured to reside within the delivery catheter and have a sufficient length to have its external end to be outside the body of the subject during device implantation.

Also featured within the housing 90 is the second channel 98 with a similarly curved distal end containing a movable plurality of individual electrodes 97, initially residing entirely within the bounds of the housing 90. Advancement of the electrodes 97 within the second channel 98 may be controlled by a second pusher 99, which may be similarly releasably attached to the plurality of electrodes 97. The other end of the second pusher may traverse the delivery catheter in parallel with the first pusher 96 and emerge outside the body of the subject to facilitate remote activation of the individual electrodes 97. As can be appreciated by those skilled in the art, individual electrodes 97 are operably connected with the circuitry of the leadless pacemaker 90 (not shown in the drawings) so as to preserve the rhythm management functionality thereof after implantation.

Upon positioning of the leadless pacemaker 90 adjacent to the cardiac tissue in the target area such as for example at the His bundle 3, the first pusher may be activated and used to advance the fixation screw 95 around the curve 93 of the channel 91—so as to cause the fixation screw 95 to emerge from within the pacemaker 90 and engage with the cardiac tissue 3. Advancement of the fixation screw 95 may be conducted until it is prevented from further movement by the mechanical stop 94.

In a similar fashion, the plurality of individual electrodes 97 may be advanced along the channel 98 by the second pusher 99—so as to cause the distal ends of the individual electrodes 97 to emerge from within the pacemaker 90 and penetrate into the cardiac tissue 3 underneath thereof. The length and individual directions of the individual electrodes 97 may be selected to assure thereof reaching desired depths and width of distribution within the target area in the heart.

Once both the fixation screw 95 and the individual electrodes 97 are positioned to engage with the adjacent cardiac tissue, the first pusher 96 and the second pusher 99 may be disengaged and removed.

Figure 31:
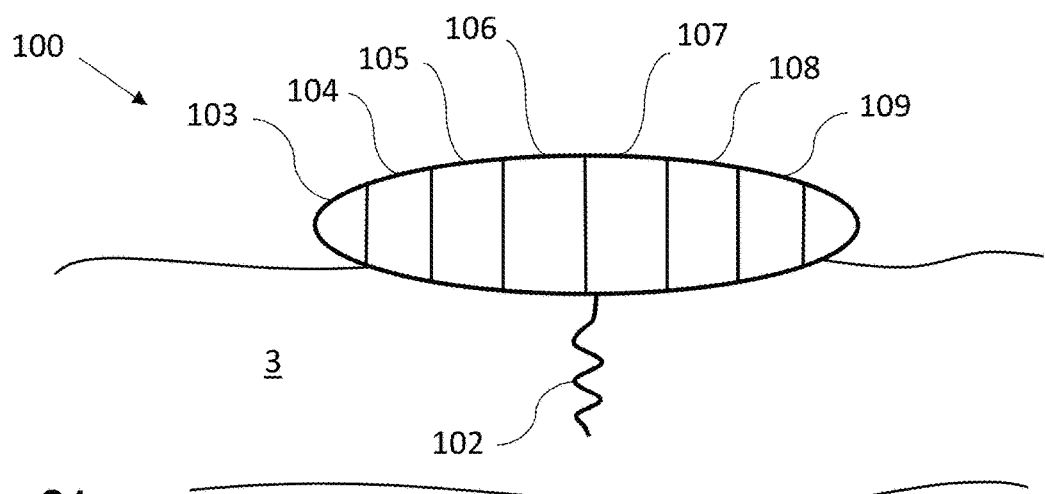
FIG. 31 is a side view of a further yet configuration of the invention with the leadless pacemaker featuring a plurality of electrode zones.

Another yet design of the leadless pacemaker of the present invention featuring a number of individual electrodes is shown in FIG. 31. In this case, the leadless pacemaker 100 may be secured to the underlying cardiac tissue 3 with a fixation screw 102 so as to position the pacemaker in close contact with the heart. The housing of the pacemaker 100 may be divided into individual electrically active zones 103-110, each zone may be activated individually by the electronic circuitry of the device so as to serve as an individual electrode. Such individual zones may be electrically isolated from one another so as to not cause electrical interference therebetween. One advantage of this design is that the exact location and spacing between individual zones is known in advance to sensing and pacing signals may be generated using this geometrical knowledge, which may not be well defined in at least some of the other embodiments of the present invention.

Figure 32:
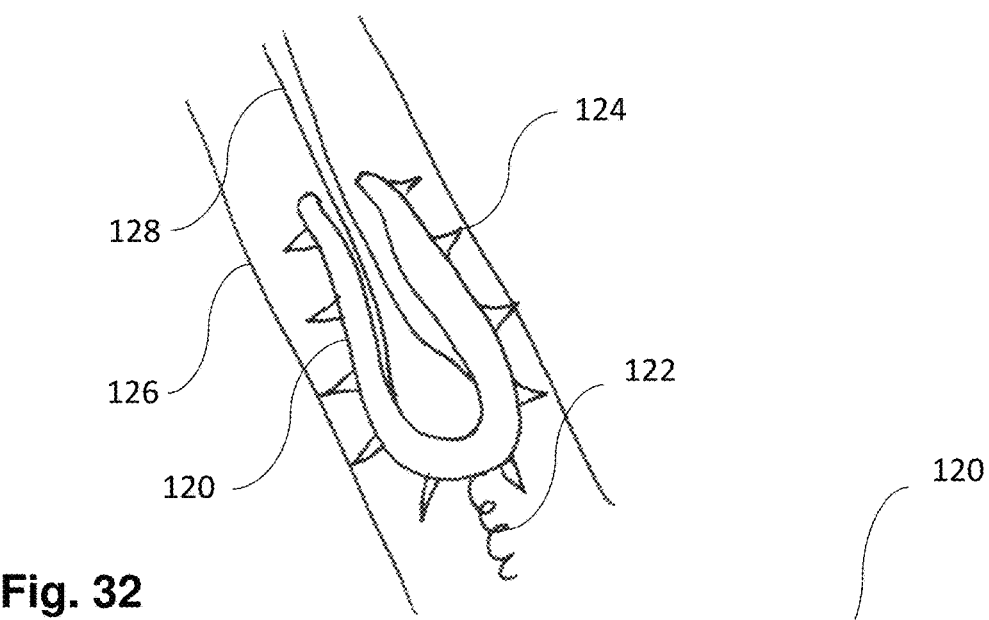
FIG. 32 shows a side view of yet another embodiment of the leadless pacemaker of the present invention while in a deployment sheath.
Figure 33:
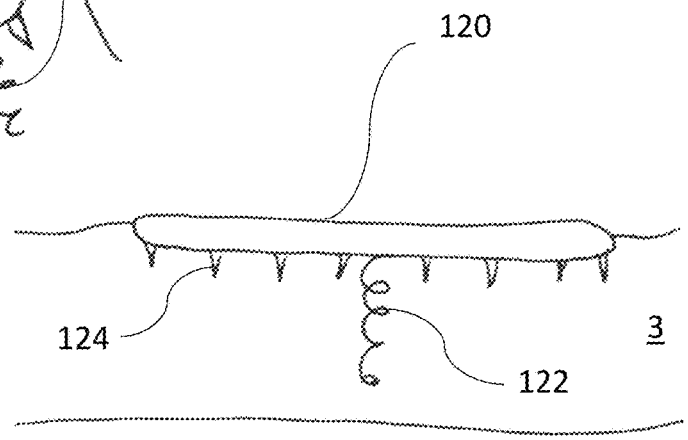
FIG. 33 shows the same as in FIG. 32 but with the leadless pacemaker of the invention shown in its final deployment position.

Another yet embodiment of the leadless pacemaker is seen in FIG. 32 (during deployment) and FIG. 33 (after implantation is complete). The housing 120 of the pacemaker may, in this case, be made to be elongated and capable of folding in its central portion. For example, the housing 120 may be made using a flexible biocompatible polymer such as silicone or polyurethane with embedded electronic components such as a battery, central processor chip etc. which may be connected to flexible circuits. The housing 120 may also feature sharp protrusions 124 configured for penetrating under the surface of the cardiac tissue upon implantation thereof.

During deployment, the leadless pacemaker 120 may be first folded and placed inside the delivery catheter 126, see FIG. 32. A pusher 128 may be used to advance the pacemaker 120 forward and activate the fixation screw 122. Once the pacemaker 120 emerges from the distal end of the delivery catheter 126, the housing 120 is allowed to extend into a straight configuration and the fixation screw 122 may be used to secure it in place at the target area. The pacemaker 120 may also be made with a malleable housing which can be pre-shaped into a preferred shape configuration based on anatomical features specific to a particular subject.

Adapter for Using a Conventional Pacemaker

In yet more embodiments of the invention, the novel leadless pacemaker may be configured to utilize an existing pacemaker, which may be already in use by the subject as a source of stimulation signals, while providing additional components to conduct this stimulation at the target area of the heart.

Figure 34:
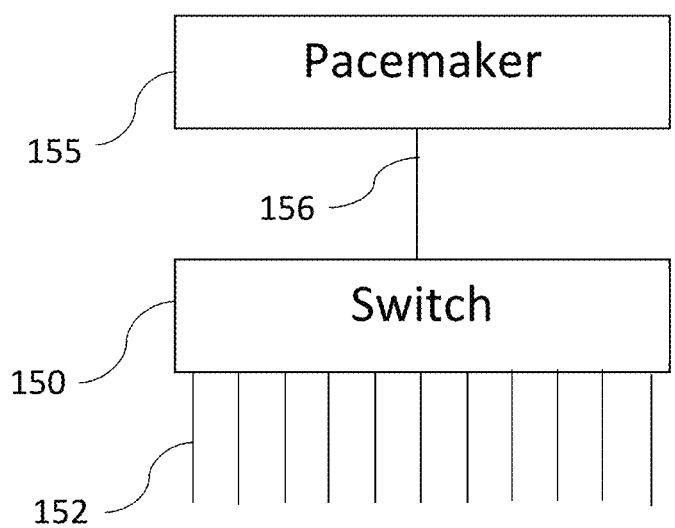
FIG. 34 shows a block diagram of another embodiment of the present invention configured for using a conventional leadless or traditional pacemaker as a source of pacing signals for the purposes of a multi-electrode pacing of the present invention.

In a broad sense, an existing new or already used before the pacemaker (conventional or leadless) in combination with novel components described below may form a new rhythm management system of the invention. Schematically shown in FIG. 34, this arrangement may include a conventional pacemaker 155 operably connected wirelessly or via a conduit 156 to a comprehensive electronic switch 150, which in turn may be operably connected to a plurality of individual electrodes 152, located at the target area in the heart such as triangle of Koch and His bundle.

The electronic switch 150 may be located near individual electrodes 152 and may itself be enclosed in a housing similar to that described above for other embodiments of the invention. The electronic switch may include its own dedicated power supply such as a primary battery, remotely controlled operational circuitry and other components of the previously described system, with the exception of the circuitry to sense heart activity or to generate pacing stimulus signals, which in this case may be provided by a conventional pacemaker 155. In certain embodiments, the electronic switch 150 may be contained in a housing which itself is configured to accept the pacemaker 155 docked inside thereof as can be seen in certain drawings described below in more detail. The housing of the switch 150 and the pacemaker 155 may, in this case, be implanted at the target area in the heart to provide direct leadless stimulation at the triangle of Koch, His bundle and surrounding areas via its selected multiple individual electrodes 152.

Following implantation of the system and positioning of the individual electrodes 152 throughout the target area in the heart, the electronic switch may be activated and together with the pacemaker 155 operated to evaluate individual electrodes 152 for their suitability as sensing and/or pacing leads for a particular subject. Once the most suitable electrodes are identified, the electronic switch 150 may be remotely operated to connect the selected individual electrodes 152 to the pacemaker 155 for subsequent operation as set by the operator. The electronic switch 150 may also be operated again from time to time to adjust the selection of the most suitable individual electrodes 152 if the circumstances change and such adjustment is needed.

The advantage of this hybrid configuration is in use of conventional and time-proven cardiac pacemaker technology, which in this case does not have to be proven out via large, long-term clinical studies. While the functionality of the electronic switch 150 is a novel element requiring proper verification, the overall technical risk and expense associated with its development may be lower than when developing a brand new cardiac rhythm management system. Therefore, this configuration may be in some cases more attractive as an initial configuration to prove out the concepts behind this invention.

Another advantageous configuration of this embodiment is when the electronic switch 150 is located outside the body of the subject and is connected to individual electrodes 152 by an extended flexible conduit. This is preferred for example when conducting animal tests so that a conventional pacemaker 155 may be easily switched to sense and/or deliver pacing pulses to a variety of individual electrodes during the course of such experiment.

The approach of repurposing the conventional pacemaker into the pacemaker of the present invention is even more advantageous when used with conventional leadless pacemakers. In this case, the entire system including a conventional pacemaker together with a miniaturized electronic switch may be implanted in the vicinity of the target area to provide the subject with a leadless rhythm management therapy which may not be achieved with a conventional leadless pacemaker alone. This concept of repurposing a conventional pacemaker may also allow providing more physiologic stimulation of the His bundle in subjects with atrial fibrillation who do not require atrial pacing and sensing but will benefit hemodynamically from His pacing rather than RV apical pacing. This allows making the existing leadless pacemaker instantaneously more physiologic. Furthermore, the same approach may also be used to pace the Left Bundle Branch (LBB) in subjects with atrial fibrillation, LBB block and cardiomyopathy who also do not require atrial pacing. The existing leadless pacemaker may, in this case, be implanted with the adapter of the invention into LBB and provide cardiac resynchronization therapy.

Figure 35:
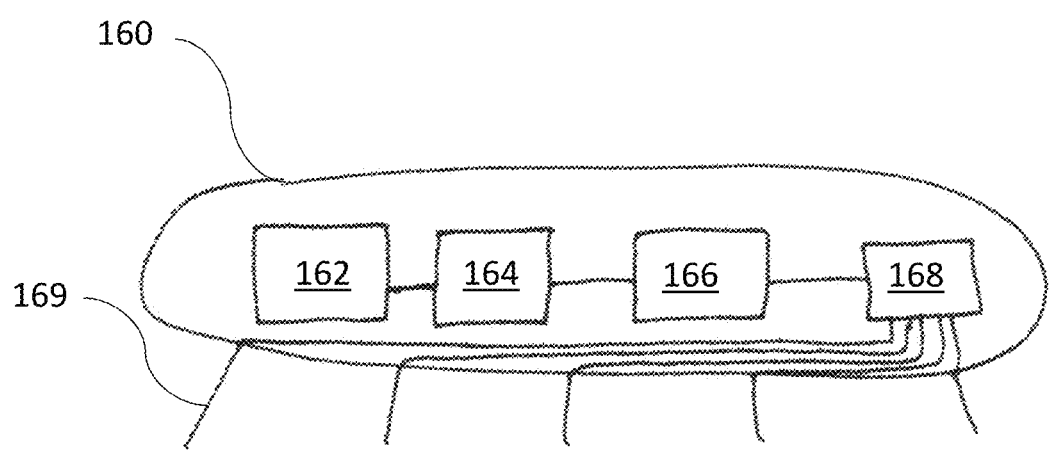
FIG. 35 shows a schematic cross-section of the embodiment of the present invention equipped with a switch to change electrode configuration remotely.

FIG. 35 shows a schematic diagram of such arrangement in which the housing 160 may be configured to retain therein or mechanically attach to a conventional leadless pacemaker 162, which may be configured to operably connect to the electronic switch 164, powered by its own dedicated power supply 166 so that together with the pacemaker 162 they can produce a system of sensing and stimulation signals that can be passed through circuitry 168 onto corresponding selected electrodes 169.

Figure 36:
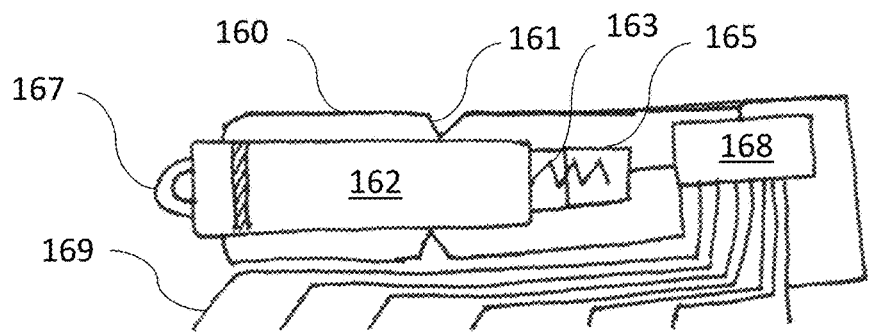
FIG. 36 shows an exemplary cross-sectional view of an embodiment of the present invention comprising the conventional single-lead pacemaker and a novel adapter for use thereof for the purposes of multi-electrode pacing.

In an exemplary embodiment shown in FIG. 36, a generally cylindrical housing 160 may feature a retaining notch 161 configured to snugly fit over the conventional leadless pacemaker 162 and retain thereof inside the housing 160. The notch 161 in certain embodiments may also provide an electrical connection between the pacemaker 162 and the housing 160. The active electrode 163 of the pacemaker 162 may be retained and operatively connected to the receptacle 165 so that both anode and cathode electrodes of the leadless pacemaker 162 are placed in operable connection with the circuitry 168, which in turn is operably connected to the plurality of individual electrodes 169.

In embodiments, the arrangement described above may have sufficient power reserve for both the pacemaker 162 and separately for the electronic switch 168 to provide cardiac rhythm management therapy for sufficient period of time. At the same time, this arrangement may be advantageously used to replace at least some components of the system in case of a power failure or some other malfunction. To achieve this, the pacemaker 162 may be equipped with the engagement and retrieval loop 167, which can be used to disconnect the pacemaker 162 from the housing 160 and replace it with a new pacemaker 162.

Figure 37:
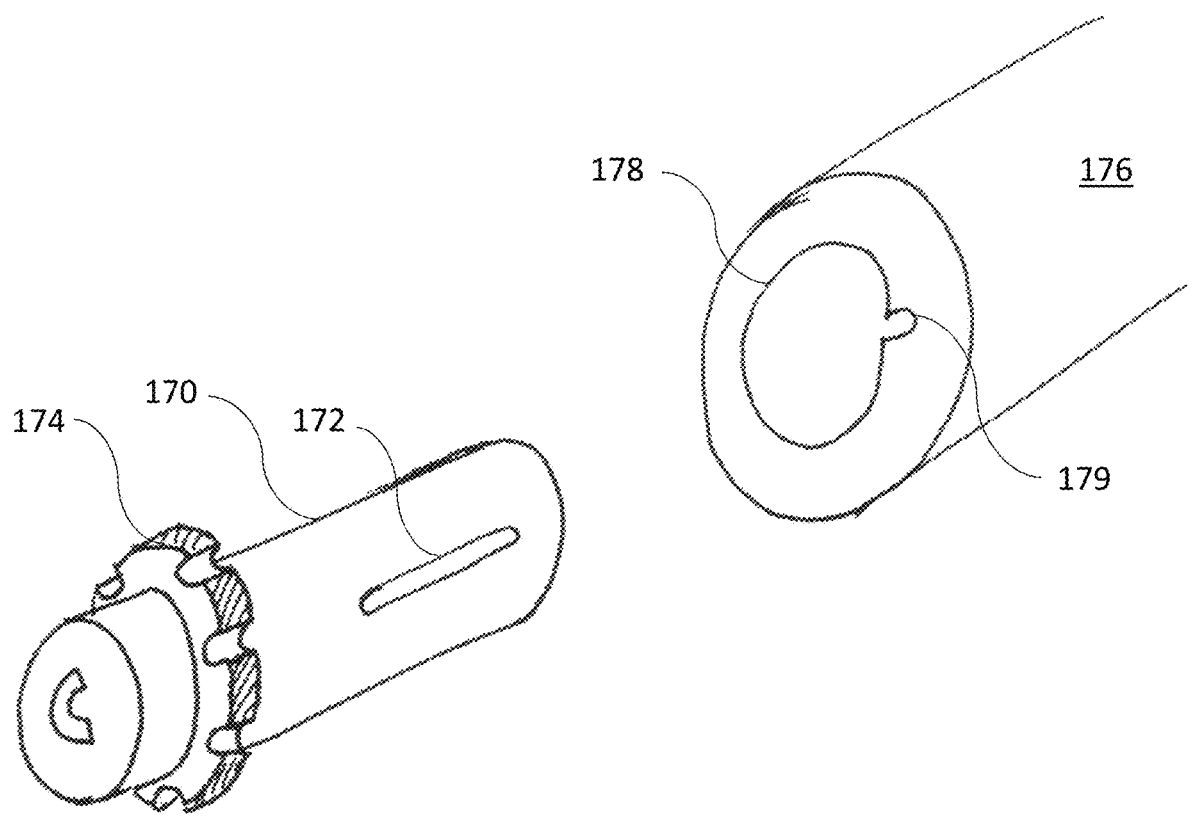
FIG. 37 shows a leadless cardiac pacemaker with a selector switch configured to connect thereof to the selected electrodes after implantation and evaluation of such electrodes prior to insertion thereof.

Finally, as an alternative to an electronic switch of the previous embodiments, a mechanical selector may be used to select the configuration of individual electrodes for use in a cardiac rhythm management therapy. This embodiment is seen in FIG. 37. In this case, the adapter 176 with a multitude of individual electrodes may be first implanted at the target area of the heart. Wired or optionally wireless communication may be used to interrogate individual electrodes of the adapter 176 and select the preferred group of electrodes for use in the delivery of the rhythm management therapy. The leadless pacemaker 170 may have a selector switch 174 that can rotate about its housing so as to configure the pacemaker 170 for operating selected electrodes of the adapter 176. Turning the selector ring 174 to the right position may be followed by implantation of the pacemaker 170 and operatively docking it with the adapter 176 by inserting it into the opening 178 such that the key 172 fits inside the groove 179—to assure the proper orientation of the pacemaker 170 inside the adapter 176.

It is contemplated that any embodiment discussed in this specification can be implemented with respect to any method of the invention, and vice versa. It will be also understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference. Incorporation by reference is limited such that no subject matter is incorporated that is contrary to the explicit disclosure herein, no claims included in the documents are incorporated by reference herein, and any definitions provided in the documents are not incorporated by reference herein unless expressly included herein.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), propertie(s), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, Aft BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12, 15, 20 or 25%.

All of the devices and/or methods disclosed and claimed herein can be made and executed without undue experimentation in light of the present disclosure. While the devices and methods of this invention have been described in terms of preferred embodiments, it will be apparent to those of skill in the art that variations may be applied to the devices and/or methods and in the steps or in the sequence of steps of the method described herein without departing from the concept, spirit and scope of the invention. All such similar substitutes and modifications apparent to those skilled in the art are deemed to be within the spirit, scope, and concept of the invention as defined by the appended claims.

What is claimed is:

1. A leadless cardiac pacemaker comprising:
    a housing configured to be implanted entirely within a single heart chamber at a predetermined target area,
    a plurality of individual electrodes located on or extending from the housing, said individual electrodes are laterally spaced apart and configured for delivering electrical stimuli to capture and pace the heart, at least some of said plurality of individual electrodes are further configured to sense electrical activity of the heart at said target area,
    a controller hermetically sealed within said housing, said controller configured to operate in succession of the following two modes following implantation of the leadless cardiac pacemaker and deployment of said plurality of individual electrodes in laterally spaced apart pattern at said target area:

an individual electrodes evaluation mode, wherein said controller is operated to interrogate each of said individual electrodes to determine a first subset of selected individual electrodes meeting a predetermined criteria for pacing a first chamber of the heart, and a second subset of selected individual electrodes for pacing a second chamber of the heart, and a therapeutic mode, wherein said controller is operated to deliver said electrical stimuli via said first subset of selected individual electrodes and said second subset of individual electrodes to capture and pace said first chamber and respectively said second chamber of the heart at said target area.

2. The leadless cardiac pacemaker as in claim 1, wherein said controller is further configured to abandon non-selected individual electrodes after operating in said evaluation mode, whereby the number of selected individual electrodes used for cardiac capture and pacing is less than the number of individual electrodes of said plurality of individual electrodes.

3. The leadless cardiac pacemaker as in claim 1, wherein said plurality of individual electrodes include between 2 and 16 individual electrodes.

4. The leadless cardiac pacemaker as in claim 1, wherein said controller is further configured while in said individual electrode evaluation mode to select at least one individual electrode suitable for atrial pacing and select at least one other individual electrode suitable for ventricular pacing via delivering of electrical stimuli to His bundle.

5. The leadless cardiac pacemaker as in claim 1, wherein said controller is further configured to deliver electrical stimuli to cause cardiac capture and pacing of multiple heart chambers from a single intra-cardiac location.

6. The leadless cardiac pacemaker as in claim 1, wherein said controller comprising a sensing circuitry configured to acquire electrical signals from one or more of said individual electrodes to monitor electrical activity of the heart.

7. The leadless cardiac pacemaker as in claim 1, wherein said predetermined criteria is selected from a group consisting of: (i) appearance of an acceptable paced P-wave on an ECG tracing when said therapeutic mode is delivered to correct an atrial conduction disturbance, (ii) selective capture of the bundle of His and/or triangle of Koch, (iii) non-selective capture of the bundle of His and/or triangle of Koch, (iv) appearance of an acceptable QRS complex on the ECG tracing when said therapeutic mode is delivered to correct atrio-ventricular, atrial, or ventricular conduction disturbances.

8. A method for providing cardiac rhythm management therapy using the leadless cardiac pacemaker as in claim 1, said method comprising the following steps:

a. implanting said leadless cardiac pacemaker at a target area defined by triangle of Koch, His bundle and surrounding areas, whereby said target area including a location suitable for pacing of a cardiac atrium and a location suitable for pacing of a cardiac ventricle of the heart, thereby positioning said laterally spaced apart individual electrodes throughout said target area such that more than one of said plurality of individual electrodes is placed at said location suitable for pacing of the cardiac atrium or at said location suitable for pacing of the cardiac ventricle of the heart, b. operating said leadless cardiac pacemaker in said individual electrodes evaluation mode for interrogating each individual electrode positioned at said location for pacing of the cardiac atrium using a predetermined criteria to select at least one individual electrode capable of capturing and pacing of the cardiac atrium, and interrogating each individual electrode positioned at said location for pacing of the cardiac ventricle to select at least one electrode capable of capturing and pacing of said cardiac ventricle via stimulation of said bundle of His, and c. operating said controller in the therapeutic mode to deliver atrial pacing and ventricular pacing via said respective selected individual electrodes from a single intra-cardiac location.

9. The method as in claim 8, wherein said step (b) further comprising sensing electrical activity of the heart using at least one or more of said individual electrodes.

10. The method as in claim 8, wherein said step (b) further comprising a step of abandoning non-selected individual electrodes and not using thereof for atrial or ventricular pacing in step (c).

11. The method as in claim 8, wherein said step (b) is repeated from time to time to select most suitable individual electrodes using said predetermined criteria.

12. The method as in claim 8, wherein said step (a) further comprising a step of implantation of a fixation screw at or near said target area followed by a step of implantation of said housing sliding along an activation wire removably attached to said fixation screw.

13. The method as in claim 8, wherein said step (a) further comprising a step of providing a delivery catheter with a foldable suction cup at a distal end thereof, expanding and positioning said suction cup at said target area, applying vacuum to temporarily affix said suction cup to said target area, and advancing said leadless cardiac pacemaker within said delivery catheter until reaching said target area.

14. The leadless cardiac pacemaker as in claim 1, further comprising a first fixation screw for securing thereof to said cardiac tissue.

15. The leadless cardiac pacemaker as in claim 14, wherein said first fixation screw is configured for operating as one of said plurality of individual electrodes and is made with sufficient length to reach His bundle upon implantation at said target area.

16. The leadless cardiac pacemaker as in claim 14, further comprising a second fixation screw, at least one or both said first fixation screw and said second fixation screw are configured to operate as individual electrodes of said plurality of individual electrodes, said first fixation screw is sufficiently long to reach left bundle branch or said second fixation screw is sufficiently long to reach right bundle branch upon implantation of said leadless cardiac pacemaker at said target area.

17. The leadless cardiac pacemaker as in claim 1, further comprising a disk-shaped flexible member containing said housing and said plurality of individual electrodes encapsulated therein, said individual electrodes exposed on one side of said flexible member and configured to stay in permanent contact with said cardiac tissue upon implantation of said leadless cardiac pacemaker.

18. The leadless cardiac pacemaker as in claim 17, wherein at least some individual electrodes are operably connected to individual extension wires or fixation screws, said individual extension wires or fixation screws are configured to penetrate said cardiac tissue to sufficient depth to provide electrical connections between said cardiac tissue and said controller suitable for delivering electrical stimuli to said cardiac tissue in a therapeutic mode of operation of said controller.

19. The leadless cardiac pacemaker as in claim 17, wherein said housing comprising a hermetically sealed first housing portion and a hermetically sealed second housing portion, said plurality of individual electrodes divided into a first plurality of individual electrodes affixed to said first housing portion and a second plurality of individual electrodes affixed to said second housing portion, said first plurality of individual electrodes slidably residing in a corresponding second plurality of channels in said second housing portion, said second plurality of individual electrodes slidably residing in a corresponding first plurality of channels in said first housing portion, said first housing portion and said second housing portion defining a collapsed position of said housing, in which none of the individual electrodes are protruding beyond the bounds of the housing.

20. The leadless cardiac pacemaker as in claim 19, wherein said first housing portion and said second housing portion defining an expanded position of said housing in which said individual electrodes are caused to emerge from said first housing portion and said second housing portion upon moving thereof closer together.

* * * * *